(12) United States Patent
Wang et al.

(10) Patent No.: US 10,487,173 B2
(45) Date of Patent: Nov. 26, 2019

(54) FLUORINE SUBSTITUTION INFLUENCE ON BENZO[2,1,3]THIODIAZOLE BASED POLYMERS FOR FIELD-EFFECT TRANSISTOR APPLICATIONS

(71) Applicant: The Regents of the University of California, Oakland, CA (US)

(72) Inventors: Ming Wang, Goleta, CA (US); Guillermo C. Bazan, Santa Barbara, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 16/001,082

(22) Filed: Jun. 6, 2018

(65) Prior Publication Data

US 2018/0282474 A1    Oct. 4, 2018

Related U.S. Application Data

(63) Continuation-in-part of application No. 15/349,908, filed on Nov. 11, 2016.

(Continued)

(51) Int. Cl.
  *C08G 61/12* (2006.01)
  *C07D 417/14* (2006.01)
(52) U.S. Cl.
  CPC ......... *C08G 61/126* (2013.01); *C07D 417/14* (2013.01); *C08G 2261/124* (2013.01);

(Continued)

(58) Field of Classification Search
  CPC ............ C08G 61/126; C08G 2261/411; C08G 2261/71; C08G 2261/146;

(Continued)

(56) References Cited

U.S. PATENT DOCUMENTS 8,455,606 B2 * 6/2013 Zhu ................ C08G 61/123
                                               136/261
9,006,376 B2 * 4/2015 Amb ................ H01L 51/0036
                                                528/370

(Continued)

FOREIGN PATENT DOCUMENTS

WO    2014039847    3/2014
WO    2015013747    2/2015

OTHER PUBLICATIONS

Heeger, Semiconducting polymers: the Third Generation, Chem. Soc. Rev. 39, pp. 2354-2371 (2010).

(Continued)

*Primary Examiner* — William F Kraig
*Assistant Examiner* — Vicki B. Booker
(74) *Attorney, Agent, or Firm* — Gates & Cooper LLP

(57) ABSTRACT

Four conjugated copolymers with a donor/acceptor architecture including 4,4-dihexadecyl-4H-cyclopenta[1,2-b:5,4-b']dithiophene as the donor structural unit and benzo[2,1,3]thiodiazole fragments with varying degrees of fluorination have been synthesized and characterized. It has been shown that the HOMO levels were decreased after the fluorine substitution. The field-effect charge carrier mobility was similar for all polymers with less than an order of magnitude difference between different acceptor units.

21 Claims, 13 Drawing Sheets

Related U.S. Application Data

(60) Provisional application No. 62/253,975, filed on Nov. 11, 2015.

(52) U.S. Cl.
CPC .................. *C08G 2261/146* (2013.01); *C08G 2261/1412* (2013.01); *C08G 2261/1526* (2013.01); *C08G 2261/164* (2013.01); *C08G 2261/3246* (2013.01); *C08G 2261/344* (2013.01); *C08G 2261/364* (2013.01); *C08G 2261/411* (2013.01); *C08G 2261/71* (2013.01); *C08G 2261/92* (2013.01)

(58) Field of Classification Search
CPC ...... C08G 2261/1412; C08G 2261/164; C08G 2261/364; C08G 2261/344; C08G 2261/124; C08G 2261/1526; C08G 2261/3246; C08G 2261/92; C07D 417/14
See application file for complete search history.

(56) References Cited

U.S. PATENT DOCUMENTS

| | | | |
|---|---|---|---|
| 9,543,529 B2* | 1/2017 | Al-Rafia | ............... C08G 61/123 |
| 9,605,102 B2 | 3/2017 | Xiao et al. | |
| 2015/0194606 A1 | 7/2015 | Luo et al. | |
| 2017/0002125 A1* | 1/2017 | Xiao | ...................... C08F 228/06 |

OTHER PUBLICATIONS

Hsu et al., The density of states and the transport effective mass in a highly oriented semiconducting polymer: Electronic delocalization in 1D, Adv. Mater., 10.1002/adma.201502820 pp. 7759-7765 (2015).
Luo et al., General strategy for self-assembly of highly oriented nanocrystalline semiconducting polymers with high mobility, Nano Lett. 14, pp. 2764-2771 (2014).
Lee et al., Doping-Induced Carrier Density Modulation in Polymer Field-Effect Transistors, Adv. Mater., 10.1002/adma.201504307, pp. 57-62 (2015).
Van der Poll et al., Non-basic high-performance molecules for solution-processed organic solar cells, Adv. Mater. 24, pp. 3646-3649 (2012).
Sharma et al., Optical absorption spectra and energy band gap in praseodymium borophosphate glasses, J. Mater. Sci. Lett. 14, pp. 71-73 (1995).
Perez et al., Effect of backbone regioregularity on the structure and orientation of a donor-acceptor semiconducting copolymer, Macromolecules 47, pp. 1403-1410 (2014).
Patel et al., NEXAFS spectroscopy reveals the molecular orientation in blade-coated pyridal[2,1,3]thiadiazole-containing conjugated polymer thin films, Macromolecules 48, pp. 6606-6616 (2015).
Kim et al., A thienoisoindigo-naphthalene polymer with ultrahigh mobility of 14.4 cm2/V-s that substantially exceeds benchmark values for amorphous silicon semiconductors, J. Am. Chem. Soc. 136, pp. 9477-9483 (2014).
Kang et al., Record high hole mobility in polymer semiconductors via sidechain engineering, J. Am. Chem. Soc. 135, pp. 14896-14899 (2013).
Olivier et al., 25th Anniversary Article: High-Mobility Hole and Electron Transport Conjugated Polymers: How Structure Defines Function Adv. Mater., 2014, 26, pp. 2119-2136.
Yamashita et al., Transition between band and hopping transport in polymer field-effect transistors, Adv. Mater. 26, pp. 8169-8173 (2014).
Rakhmanova et al., Electric-field dependence of mobility in conjugated polymer films, Appl. Phys. Lett. 76, pp. 3822-3824 (2000).
McCulloch et al., Liquid-crystalline semiconducting polymers with high charge-carrier mobility, Nat. Mater. 5, pp. 328-333 (2006).
Cho et al., Extended lifetime of organic field-effect transistors encapsulated with titanium sub-oxide as an 'active' passivation/barrier Layer, Adv. Mater. 21, pp. 1941-1944 (2009).
Bobbert et al., Operational stability of organic field-effect transistors, Adv. Mater. 24, pp. 1146-1158 (2012).
Lee et al., Air-stable polymer electronic devices, Adv. Mater. 19, pp. 445-2449 (2007).
Chen et al., Air stable n-channel organic semiconductors for thin film transistors based on fluorinated derivatives of perylene diimides, Chem. Mater. 19, pp. 816-824 (2007).
Katz et al., A soluble and air-stable organic semiconductor with high electron mobility, Nature 404, pp. 478-481 (2000).
Arias et al., Materials and Applications for Large Area Electronics: Solution-Based ApproachesChem. Rev.,2010, 110, pp. 3-24.
Diao et al., Solution coating of large-area organic semiconductor thin films with aligned single-crystalline domains, Nat. Mater., 2013, 12, pp. 665-671.
Zhang et al., Field-Effect Transistors Based on a Benzothiadiazole-Cyclopentadithiophene Copolymer. Am. Chem. Soc., 2007, 129, pp. 3472-3473.
DeLeeuw et al., Stability of n-type doped conducting polymers and consequences for polymeric microelectronic devices. Synth. Met., 1997, 87, pp. 53-59.
Zhang et al., Indacenodithiophene Semiconducting Polymers for High-Performance, Air-Stable Transistors. J. Am. Chem. Soc., 2010, 132, pp. 11437-11439.
Cardona et al., Electrochemical Considerations for Determining Absolute Frontier Orbital Energy Levels of Conjugated Polymers for Solar Cell Applications. Adv. Mater., 2011, 23, pp. 2367-2371.
Zaumseil et al., Electron and Ambipolar Transport in Organic Field-Effect Transistors. Chem. Rev., 2007, 107, pp. 1296-1323.
Zhao et al., 25th Anniversary Article: Recent Advances in n-Type and Ambipolar Organic Field-Effect Transistors. Adv. Mater., 2013, 25, pp. 5372-5391.
Venkateshvaran et al., Approaching disorder-free transport in high-mobility conjugated polymers. Nature, 2014, 515, pp. 384-388.
Liu et al., High Thermal Stability Solution-Processable Narrow-Band Gap Molecular Semiconductors. J. Am. Chem. Soc., 2014, 136, pp. 16144-16147.
Bronstein et al., Effect of Fluorination on the Properties of a Donor-Acceptor Copolymer for Use in Photovoltaic Cells and Transistors. Chem. Mater., 2013, 25, pp. 277-285.
Rivnay et al., Quantitative Determination of Organic Semiconductor Microstructure from the Molecular to Device Scale. Chem. Rev., 2012, 112, pp. 5488-5519.
Chabinyc et al., X-ray Scattering from Films of Semiconducting Polymers. Polym. Rev., 2008, 48, pp. 463-492.
Tseng et al. "High Mobility Field Effect Transistors Based on Macroscopically Oriented, Regioregular Copolymers", Nano Letters, vol. 12, iss. 12, pp. 6353-6357, 2012.
Tseng et al. "High Mobility Field Effect Transistors Fabricated with Macroscopic Aligned Semiconducting Polymers", Advanced Materials, pp. 1-6, 2014.
Zhang et al., "Significant Improved Performance of Photovoltaic Cells Made from a Partially Fluorinated Cyclopentadithiophene/Benzothiadiazole Conjugated Polymer". Macromolecules, 2012, 45, pp. 5427-5435.
Ying et al., "Regioregular Pyridal[2, 1,3]thiadiazole π-Conjugated Copolymers". J. Am. Chem. Soc., 2011, 133, pp. 18538-18541.

* cited by examiner

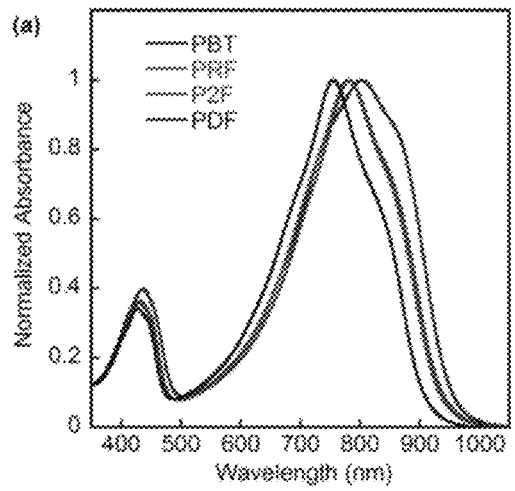
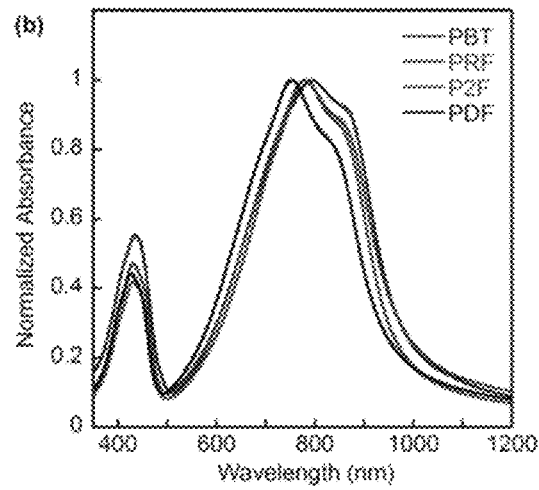
*Fig. 2(a)*     *Fig. 2(b)*
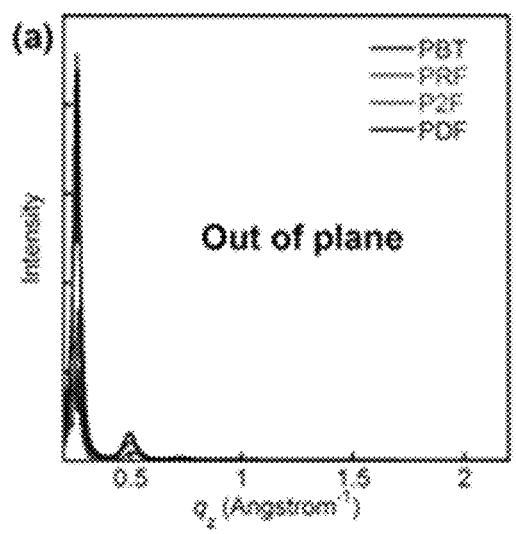
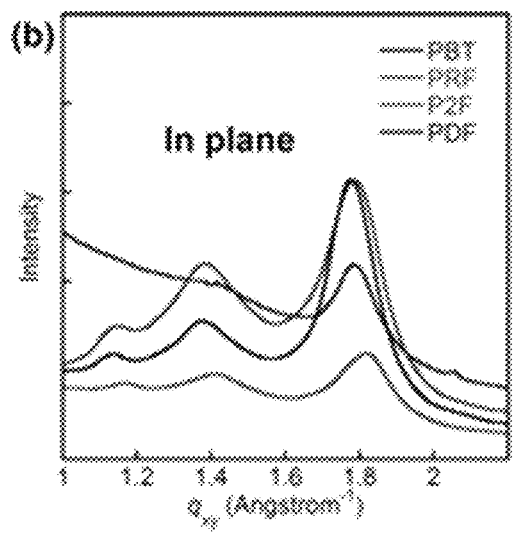
*Fig. 2(c)*     *Fig. 2(d)*

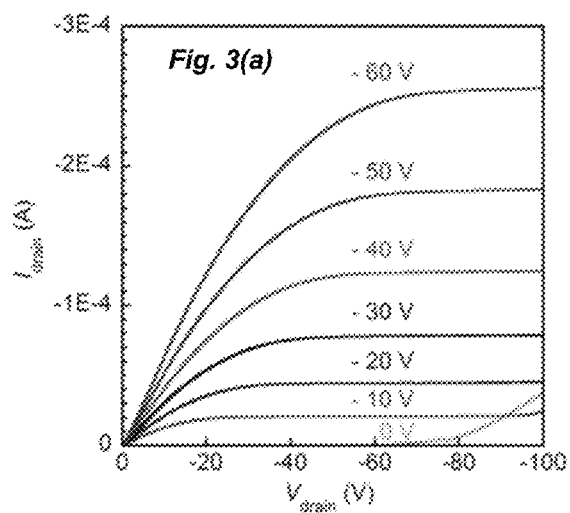
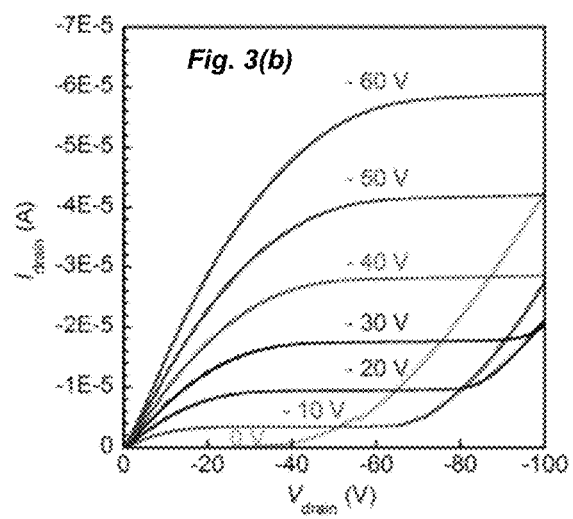
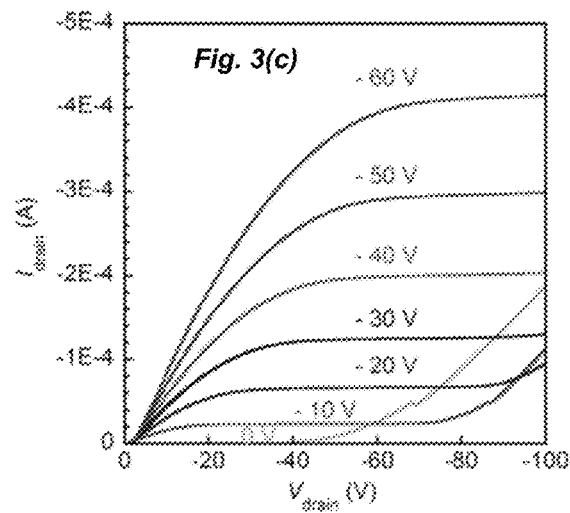
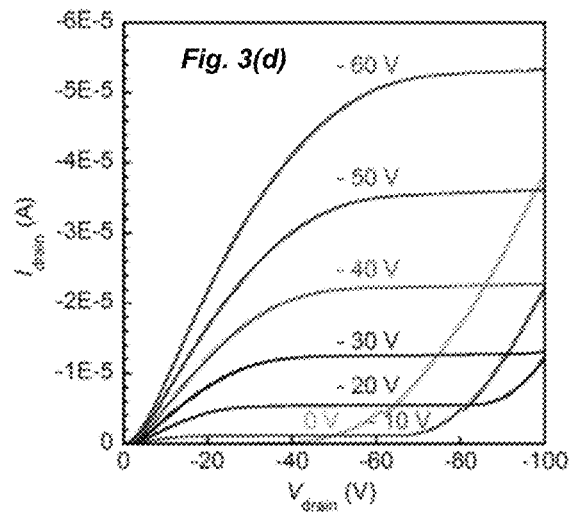

FLUORINE SUBSTITUTION INFLUENCE ON BENZO[2,1,3]THIODIAZOLE BASED POLYMERS FOR FIELD-EFFECT TRANSISTOR APPLICATIONS

CROSS REFERENCE TO RELATED APPLICATIONS

This application is a continuation-in-part under 35 U.S.C. Section 120 of co-pending and commonly-assigned Utility application Ser. No. 15/349,908, filed on Nov. 11, 2016, by Ming Wang and Guillermo Bazan, entitled "FLUORINE SUBSTITUTION INFLUENCE ON BENZO[2,1,3]THIODIAZOLE BASED POLYMERS FOR FIELD-EFFECT TRANSISTOR APPLICATIONS," which application claims the benefit under 35 U.S.C. Section 119(e) of commonly-assigned U.S. Provisional Patent Application No. 62/253,975, filed Nov. 11, 2015, by Ming Wang and Guillermo Bazan, entitled "FLUORINE SUBSTITUTION INFLUENCE ON BENZO[2,1,3]THIODIAZOLE BASED POLYMERS FOR FIELD-EFFECT TRANSISTOR APPLICATIONS,";

which applications are incorporated by reference herein.

This application claims the benefit under 35 U.S.C. Section 119(e) of commonly-assigned U.S. Provisional Patent Application No. 62/214,076, filed Sep. 3, 2015, by Byoung Hoon Lee and Alan J. Heeger, entitled "DOPING-INDUCED CARRIER DENSITY MODULATION IN POLYMER FIELD-EFFECT TRANSISTORS,", which application is incorporated by reference herein.

This application is related to the following commonly-assigned U.S. patent applications:

U.S. Provisional Patent Application No. 62/367,401, filed Jul. 27, 2016, by Colin R. Bridges, Michael J. Ford, Guillermo C. Bazan, and Rachel A. Segalman, entitled "FORMATION AND STRUCTURE OF LYOTROPIC LIQUID CRYSTALLINE MESOPHASES IN DONOR-ACCEPTOR SEMICONDUCTING POLYMERS,";

U.S. Provisional Patent Application No. 62/338,866, filed May 19, 2016, by Michael J. Ford, Hengbin Wang, and Guillermo Bazan, entitled "ORGANIC SEMICONDUCTOR SOLUTION BLENDS FOR SWITCHING AMBIPOLAR TRANSPORT TO N-TYPE TRANSPORT,";

U.S. Provisional Patent Application No. 62/327,311, filed Apr. 25, 2016, by Guillermo Bazan and Ming Wang, entitled "NOVEL WEAK DONOR-ACCEPTOR CONJUGATED COPOLYMERS FOR FIELD-EFFECT TRANSISTOR APPLICATIONS,";

U.S. Provisional Patent Application No. 62/276,145, filed Jan. 7, 2016, by Michael J. Ford and Guillermo Bazan, entitled "STABLE ORGANIC FIELD-EFFECT TRANSISTORS BY INCORPORATING AN ELECTRON-ACCEPTING MOLECULE,";

U.S. Utility patent application Ser. No. 15/256,160, filed Sep. 2, 2016, by Byoung Hoon Lee and Alan J. Heeger, entitled "DOPING-INDUCED CARRIER DENSITY MODULATION IN POLYMER FIELD-EFFECT TRANSISTORS,", which application claims the benefit under 35 U.S.C. Section 119(e) of commonly-assigned U.S. Provisional Patent Application No. 62/214,076, filed Sep. 3, 2015, by Byoung Hoon Lee and Alan J. Heeger, entitled "DOPING-INDUCED CARRIER DENSITY MODULATION IN POLYMER FIELD-EFFECT TRANSISTORS,";

U.S. Utility patent application Ser. No. 15/241,949 filed Aug. 19, 2016, by Michael Ford and Guillermo Bazan, entitled "HIGH MOBILITY POLYMER ORGANIC FIELD-EFFECT TRANSISTORS BY BLADE-COATING SEMICONDUCTOR: INSULATOR BLEND SOLUTIONS,", which application claims the benefit under 35 U.S.C. Section 119(e) of U.S. Provisional Patent Application No. 62/207,707, filed Aug. 20, 2015, by Michael Ford and Guillermo Bazan, entitled "HIGH MOBILITY POLYMER ORGANIC FIELD-EFFECT TRANSISTORS BY BLADE-COATING SEMICONDUCTOR: INSULATOR BLEND SOLUTIONS,"; and U.S. Provisional Patent Application No. 62/262,025, filed Dec. 2, 2015, by Michael Ford and Guillermo Bazan, entitled "HIGH MOBILITY POLYMER ORGANIC FIELD-EFFECT TRANSISTORS BY BLADE-COATING SEMICONDUCTOR: INSULATOR BLEND SOLUTIONS,";

U.S. Utility application Ser. No. 15/213,029 filed on Jul. 18, 2016 by Byoung Hoon Lee and Alan J. Heeger, entitled "FLEXIBLE ORGANIC TRANSISTORS WITH CONTROLLED NANOMORPHOLOGY", which application claims the benefit under 35 U.S.C. Section 119(e) of U.S. Utility U.S. Provisional Application Ser. No. 62/193,909 filed on Jul. 17, 2015 by Byoung Hoon Lee and Alan J. Heeger, entitled "FLEXIBLE ORGANIC TRANSISTORS WITH CONTROLLED NANOMORPHOLOGY";

U.S. Utility patent application Ser. No. 15/058,994, filed Mar. 2, 2016, by Shrayesh N. Patel, Edward J. Kramer, Michael L. Chabinyc, Chan Luo and Alan J. Heeger, entitled "BLADE COATING ON NANOGROOVED SUBSTRATES YIELDING ALIGNED THIN FILMS OF HIGH MOBILITY SEMICONDUCTING POLYMERS,", which Application claims the benefit under 35 U.S.C. Section 119(e) of U.S. Provisional Patent Application No. 62/127,116, filed Mar. 2, 2015, by Shrayesh N. Patel, Edward J. Kramer, Michael L. Chabinyc, Chan Luo and Alan J. Heeger, entitled "BLADE COATING ON NANOGROOVED SUBSTRATES YIELDING ALIGNED THIN FILMS OF HIGH MOBILITY SEMICONDUCTING POLYMERS,";

U.S. Utility patent application Ser. No. 14/585,653, filed on Dec. 30, 2014, by Chan Luo and Alan Heeger, entitled "HIGH MOBILITY POLYMER THIN FILM TRANSISTORS WITH CAPILLARITY MEDIATED SELF-ASSEMBLY", which application claims the benefit under 35 U.S.C. Section 119(e) of U.S. Provisional Patent Application Ser. No. 61/923,452, filed on Jan. 3, 2014, entitled "HIGH MOBILITY POLYMER THIN FILM TRANSISTORS WITH CAPILLARITY MEDIATED SELF-ASSEMBLY,";

U.S. Utility patent application Ser. No. 14/426,467, filed on Mar. 6, 2015, by Hsing-Rong Tseng, Lei Ying, Ben B. Y. Hsu, Christopher J. Takacs, and Guillermo C. Bazan, entitled "FIELD-EFFECT TRANSISTORS BASED ON MACROSCOPICALLY ORIENTED POLYMERS," which application claims the benefit under 35 U.S.C. § 365 of PCT International patent application Ser. No. PCT/US13/058546 filed Sep. 6, 2013, which application claims the benefit under 35 U.S.C. Section 119(e) of U.S. Provisional Patent Application Ser. Nos. 61/698,065, filed on Sep. 7, 2012, and 61/863,255, filed on Aug. 7, 2013, entitled "FIELD-EFFECT TRANSISTORS BASED ON MACROSCOPICALLY ORIENTED POLYMERS,"; and U.S. Utility patent application Ser. No. 13/526,371, filed on Jun. 18, 2012, by G. Bazan, L. Ying, B. Hsu, W. Wen, H-R Tseng, and G. Welch entitled "REGIOREGULAR PYRIDAL[2,1,3]THIADIAZOLE PI-CONJUGATED COPOLYMERS FOR ORGANIC SEMICONDUCTORS", which application claims priority under 35 U.S.C. § 119(e) to U.S. Provisional Patent Application Ser. No. 61/498,390, filed on Jun. 17, 2011, by G. Bazan, L. Ying, B. Hsu, and G. Welch entitled "REGIOREGULAR CONSTRUCTIONS FOR THE SYNTHESIS OF THIADIAZOLO (3,4) PYRIDINE CONTAINING NARROW BAND GAP CONJUGATED POLYMERS" and U.S. Provisional Patent Application Ser. No. 61/645,970, filed on May 11, 2012, by G. Bazan, L. Ying, and Wen, entitled "REGIOREGULAR PYRIDAL[2,1,3]THIADIAZOLE PI-CONJUGATED COPOLYMERS FOR ORGANIC SEMICONDUCTORS";

all of which applications are incorporated by reference herein.

BACKGROUND OF THE INVENTION

1. Field of the Invention

This invention relates to high mobility organic field effect transistors (OFETs).

2. Description of the Related Art (Note: This application references a number of different publications as indicated throughout the specification by one or more reference numbers in parentheses, e.g., (x). A list of these different publications ordered according to these reference numbers can be found below in the section entitled "References." Each of these publications is incorporated by reference herein.)

Instability of semiconducting polymers developed to date limit practical applications. One or more embodiments of the present invention overcome these problems.

SUMMARY OF THE INVENTION

One or more embodiments of the present invention describe various semiconductor polymers comprising fluorinated conjugated polymer chains, one or more methods for fabricating the semiconducting polymers, and one or more devices incorporating the semiconducting polymers.

The devices and methods are embodied in many ways, including, but not limited to, the following embodiments 1-11 listed below.

1. One or more organic field effect transistor (OFET)s each comprising a channel including semiconducting polymers, wherein each of the semiconducting polymers have a main chain section and a repeating unit of the structure:

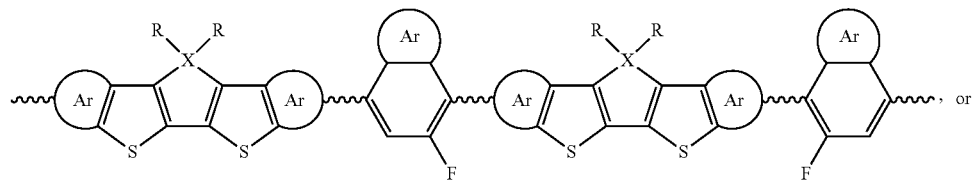

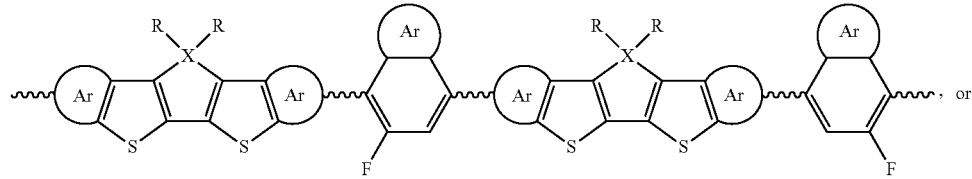

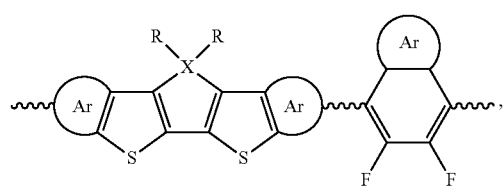

wherein each Ar is independently a substituted or non-substituted aromatic functional group, or each Ar is independently nothing and the valence of its respective ring is completed with hydrogen, each R is independently hydrogen or a substituted or non-substituted alkyl, aryl or alkoxy chain; and X is C, Si, Ge, N or P. The OFETs each further comprise a source contact to the semiconducting polymers; a drain contact to the semiconducting polymers; and a gate contact on or above the channel.

2. The OFETs of embodiment 1, wherein each of the semiconducting polymers have the repeating unit of the structure:

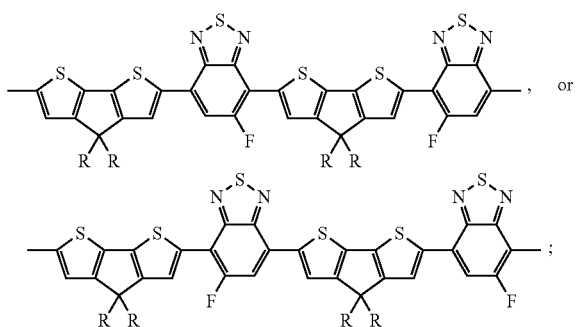

and wherein the fluorine (F) is regioregularly arranged along each of the main chain sections.

3. The OFETs of any of the preceding embodiments 1-2, wherein the semiconducting polymers are exposed to air for at least one day (24 hours).

4. The OFETs of any of the preceding embodiments 1-3, wherein carrier mobility of the OFET is at least 0.03 $cm^2V^{-1}s^{-1}$ after exposure to the air for 5 days.

5. A package comprising the OFETs of any of the preceding embodiments 1-4, wherein the package exposes the semiconducting polymers to the air for at least 5 days.

6. The OFETs of any of the preceding embodiments 1-5, wherein the OFET is encapsulated in an air permeable material such as plastic.

7. The OFETs of any of the preceding embodiments 1-6, wherein the semiconducting polymers are non-aligned (or have no clear alignment as measured in a top surface of an AFM image) and/or the semiconducting polymers are disposed on a planar, non-grooved surface, and the OFETs each have a hole mobility of at least 1.2 $cm^2V^{-1}s^{-1}$ in a saturation regime (e.g., in a range of 1.2-10 $cm^2V^{-1}s^{-1}$ in the saturation regime).

8. The OFETs of any of the preceding embodiments 1-7, wherein the semiconducting polymers are stacked into a crystalline structure, and the crystalline structure is characterized by observation of a diffraction peak measured by grazing incidence wide-angle X-ray scattering (GIWAXS) of the film.

9. The OFETs of any of the preceding embodiments 1-8, wherein a π-π distance between adjacent semiconducting polymers is no more than 0.35 nm.

10. A composition of matter comprising a polymer having the following structure:

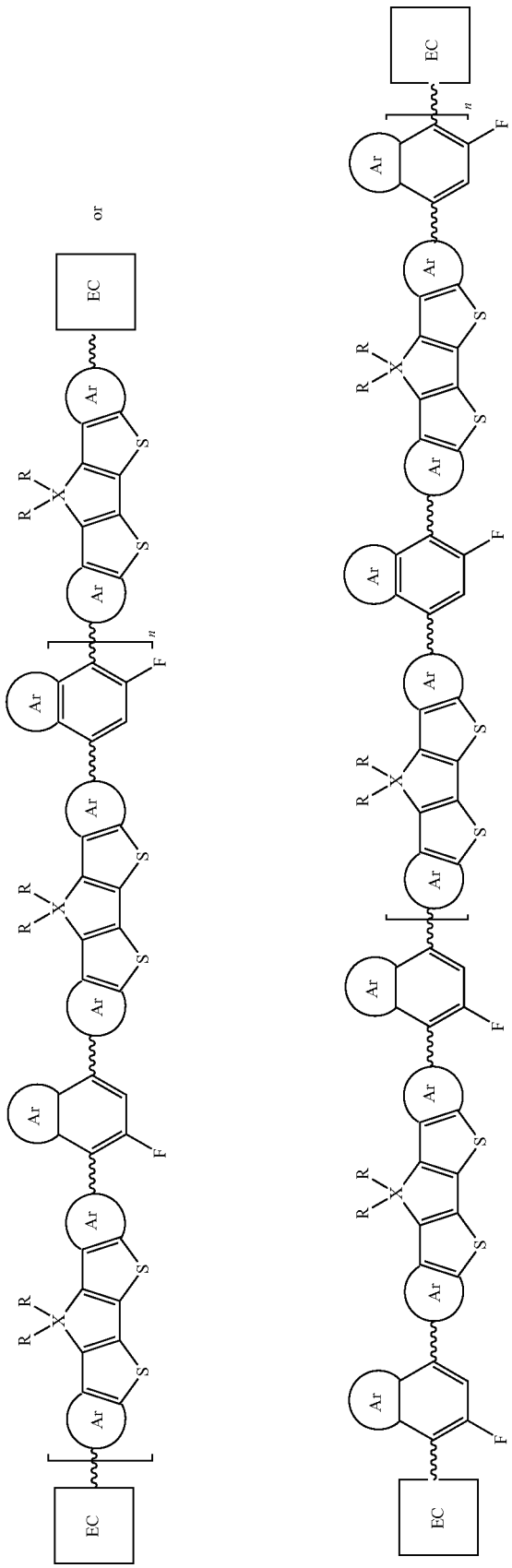

wherein Ar is a substituted or non-substituted aromatic functional group containing one, two, three or more aromatic rings, or Ar is nothing and the valence of the ring comprising fluorine (F) is completed with hydrogen, each Ar is independently a substituted or non-substituted aromatic functional group, or each Ar is independently nothing and the valence of its respective ring is completed with hydrogen, each R is independently hydrogen or a substituted or non-substituted alkyl, aryl or alkoxy chain; n is an integer; and EC is an end capping moiety.

11. The composition of matter of embodiment 10, wherein EC is an aromatic moiety 12. The composition of matter of one or any combination of embodiments 10-11, wherein the polymer comprises a palladium content of less than 200 parts per million.

13. The composition of matter of one or any combination of embodiments 10-12 wherein the polymer has a molecular weight in a range of 45-55 kilodaltons (kDa).

14. The composition of matter of one or any combination of embodiments 10-13 wherein the polymer has a molecular weight in a range of 30-80 kDa.

15. The composition of matter of one or any combination of embodiments 10-14 wherein the polymer has a molecular weight of 50 kDa.

16. An organic field effect transistor comprising a channel including the composition of matter of one or any combination of embodiments 10-15, a source contact to the channel; a drain contact to the channel; and a gate contact on or above the channel.

17. A method of fabricating a composition of matter of one or any combination of embodiments 1-16, comprising performing a coupling reaction wherein a first compound and a second compound are coupled in a solution to form a product, and the first compound comprises a dithiophene and the second compound has the structure:

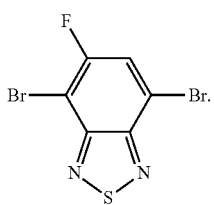 [SMILES: Fc1cc(Br)c2nsnc2c1Br]

The method further comprises purifying the product in a solvent mixture to obtain a third compound having the structure (M2):

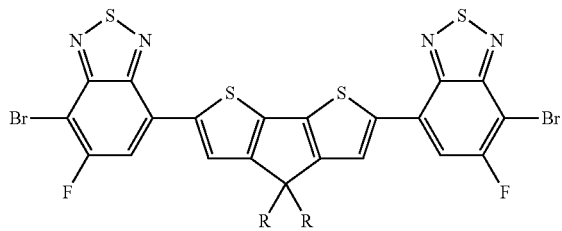

18. The method of embodiment 17 further comprising polymerizing the third compound with the first compound, wherein the first compound is a monomer of the structure (M1):

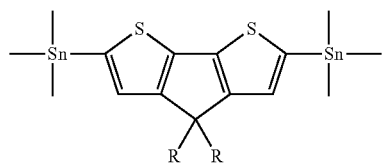

to obtain the semiconducting polymer having a repeating unit of the structure:

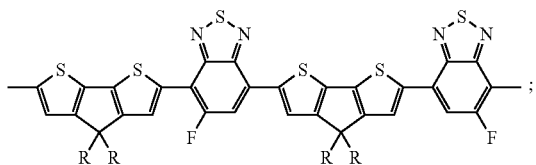

and wherein the fluorine (F) is regioregularly arranged along the semiconducting polymer's conjugated main chain section; and the R are each independently an alkyl, aryl, or an alkoxy chain.

19. The method of one or any combination of embodiments 17-18, wherein performing the coupling reaction comprises reacting an excess amount of the second compound with the first compound (M1) so as to form the third compound (M2).

20. The method of embodiment 19, wherein the excess amount is such that a ratio of the second compound to the first compound is in a range of 1.5-4:1.

21. The method of embodiment 19, wherein the excess amount is such that the ratio is between 2.2-2.5:1.

22. The method of one or any of the embodiments 17-21, wherein the coupling reaction is performed at a temperature between 50° C. to 130° C.

23. The method of one or any of the embodiments 17-21, wherein the coupling reaction is performed at a temperature between 70° C. and 110° C.

24. The method of one or any combination of embodiments 17-23 further comprising performing the polymerization using a ratio of M1:M2 of 1.15:1.

25. The method of one or any combination of embodiments 17-23, further comprising performing the polymerization using a ratio of M1:M2 of less than 1.

26. The method of one or any combination of embodiments 17-25, wherein the excess amount and a temperature at which the coupling reaction is performed, and a ratio of M1:M2 during the polymerization, are such that a percentage yield of third compound (M2) is at least 60%, a percentage yield of the polymer is at least 70%, and the polymer having a molecular weight in a range of 30-80 kDa is extracted.

27. The method of one or any combination of embodiments 17-26, further comprising performing an end-capping reaction with aromatic tin or aromatic bromide so as to obtain an end capped polymer of the structure:

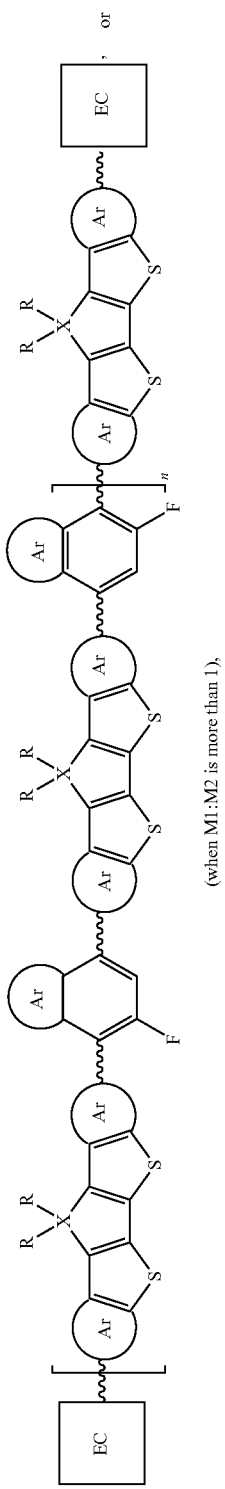
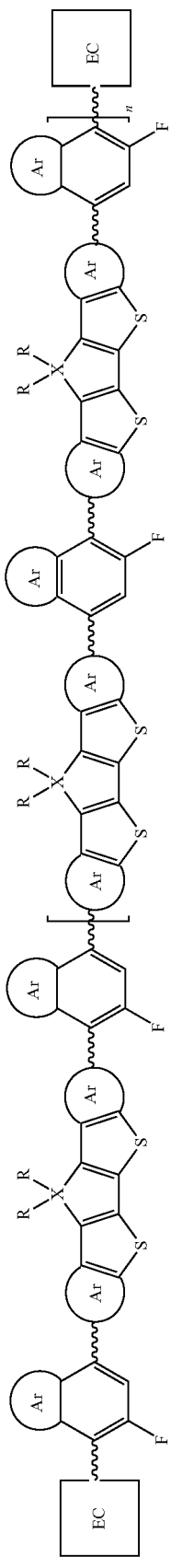

and wherein EC is the aromatic moiety of the aromatic tin or aromatic bromide.

28. The method of embodiment 27, wherein only one end-capping reagent, either an aromatic bromide or an aromatic tin, not both, is used in the end-capping reaction.

29. The composition of matter of embodiments 27 or 28, wherein the aromatic bromide is bromobenzene or bromothiophene.

30. The composition of matter of embodiment, wherein the end-capping reagent is an aromatic tin.

31. The composition of matter of claim 30, wherein the aromatic tin is trimethyltinthiophene.

32. The method of embodiment 27, wherein the end capping is in a presence of a catalyst, the method further comprising combining the end capped polymer in solution with sodium diethyldithiocarbamate aqueous solution so as to form a mixture; heating the mixture; separating an organic phase from the mixture; washing the organic phase; concentrating the organic phase; and adding the organic phase drop wise to a solvent so as to precipitate a purified form of the end capped polymer.

33. The method of embodiment 27 wherein the end capping is in a presence of a catalyst, the method further comprising passing the end capped polymer in solution through a silica gel column so as to obtain a purified solution; and adding the purified solution drop wise to a solvent so as to precipitate a purified form of the end capped polymer.

BRIEF DESCRIPTION OF THE DRAWINGS

Referring now to the drawings in which like reference numbers represent corresponding parts throughout:

FIG. 2(a) illustrates UV-vis absorption of polymers in chlorobenzene solution and FIG. 2(b) illustrates UV-vis absorption of polymers in thin films, according to one or more embodiments of the present invention.

FIG. 2(c) illustrates GIWAXS measurement out of plane line-cut profiles and FIG. 2(d) illustrates GIWAXS measurement in plane line-cut profiles, of non-aligned semiconducting polymers (or semiconducting polymers with no clear alignment as measured in a top surface of an AFM image of the semiconducting polymers) according to one or more embodiments of the present invention.

FIGS. 3(a)-3(d) illustrate output curves of four polymer devices comprising non-aligned semiconducting polymers (or semiconducting polymers with no clear alignment as measured in a top surface of an AFM image of the semiconducting polymers) according to one or more embodiments of the present invention.

DETAILED DESCRIPTION OF THE INVENTION

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Technical Description

Solution-processed OFETs are under intense investigation because of the potential they offer in terms of production costs and fabrication of flexible, light-weight substrates.[1] Saturation regime mobilities of over $10 \, cm^2 v^{-1} s^{-1}$ have been achieved through coupled developments in molecular design strategies and improvements in film processing methods.[2] Conjugated polymers containing a backbone with alternating donor-acceptor units comprise one of the most important approaches for achieving high mobility organic semiconductors used as the OFET transport material.[3] Such structures consist of an electron rich moiety (donor, D) and an electron deficient moiety (acceptor, A) in each repeat unit. For example, Müllen et al. developed a polymer containing 4,4-dihexadecyl-4H-cyclopenta[1,2-b:5,4-b']dithiophene (CDT) as the donor unit and benzo[2,1,3]thiadiazole (BT) as the acceptor unit,[4] namely PBT in Scheme 1 (CDTBTZ in the original publication), which was shown to be suitable for thin film polymer alignment thereby able to attain mobility of $6.5 \, cm^2 V^{-1} s^{-1}$.[5] The molecular structure has been further refined by substituting the BT unit with a [1,2,5]thiadiazolo[3,4-c]pyridine (PT) unit through synthetic protocols that yield regioregular backbone structures.[6] This regioregular polymer has yielded some of the highest mobilities in the literature (over $20 \, cm^2 V^{-1} s^{-1}$) through molecular weight control and novel film processing techniques that improve chain alignment.[2d]

Despite successes in achieving high charge carrier mobilities, copolymers containing CDT and BT structural units exhibit relatively high-lying highest occupied molecular orbital (HOMO) levels (−5.0±0.2 eV);[7] not an ideal situation for long-term air stability (below −5.27 eV).[8] For structures containing the more electron withdrawing PT fragments, the basic nature of the PT heterocycle can destabilize relevant electronic properties when adjacent to acidic surfaces or exposed to air.[9] Based on the above concerns, one or more embodiments of the present invention sought to design D-A copolymers containing CDT in conjunction fluorine-substituted BT derivatives as the acceptor. This approach was anticipated to lower the orbital levels of the resulting polymers and improve stability both in OFET and optoelectronic devices.[10]

I. First Embodiment: Polymers on Non-Grooved Substrates a. Fabrication

Figure 1:
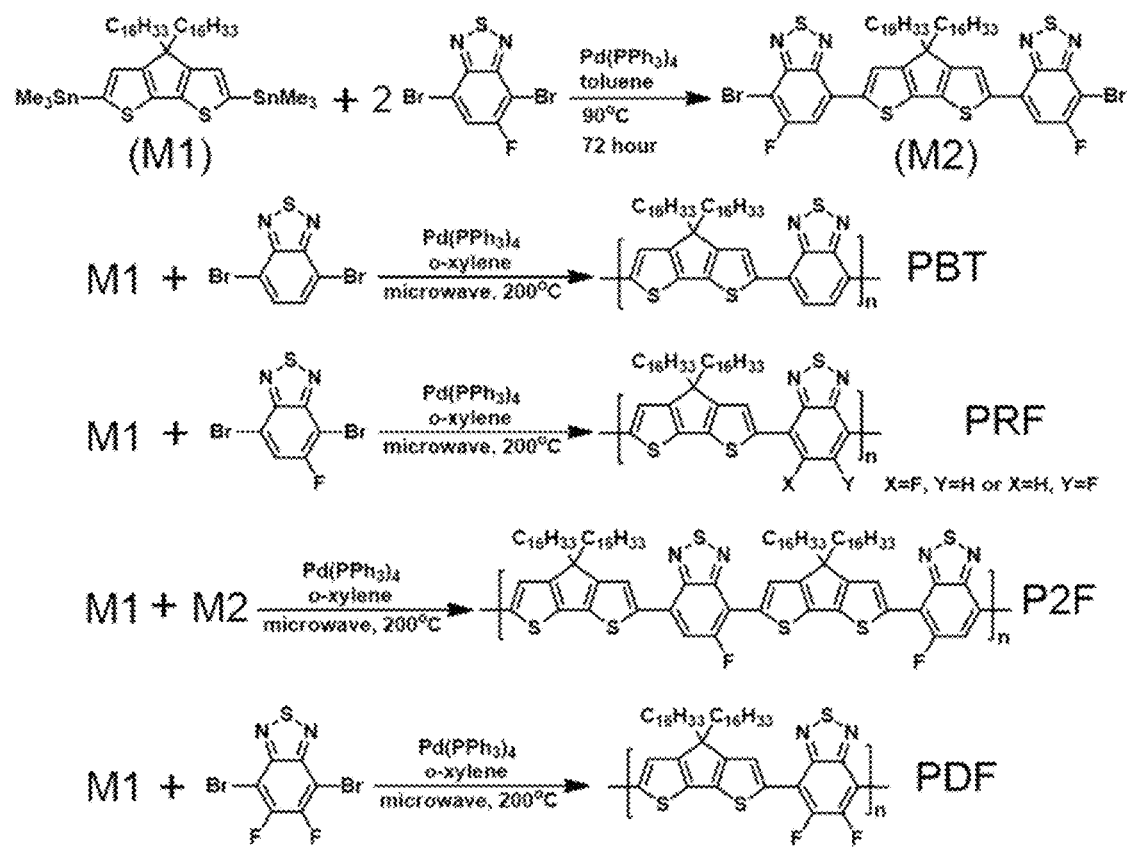
FIG. 1 illustrates a scheme for polymer synthesis according to one or more embodiments of the present invention.

The present disclosure describes synthesis of four polymers with increasing levels of fluorination and structural precision, and then studies their chemical properties, thin films feature, and application in OFETs to investigate the effects of fluorinated BT units. As shown in FIG. 1, the previously reported non-fluorinated reference polymer PBT was prepared via Stille polymerization using (4,4-dihexadecyl-4H-cyclopenta[1,2-b:5,4-b']dithiophene-2,6-diyl)bis(trimethylstannane) (M1 in Scheme 1) and 4,7-dibromobenzo[2,1,3]thiadiazole in the presence of catalytic Pd(PPh$_3$)$_4$ in anhydrous o-xylene under microwave heating (200° C.). These reaction conditions were used for all other polymer preparations. Single fluorine substitution on BT creates an asymmetric structure and raises the issue of needing to achieve a regioregular backbone for maximizing order within the chain, and ultimately between chains in the solid state.[11] Accordingly, equimolar quantities of M1 and 4,7-dibromo-5-fluorobenzo[2,1,3]thiadiazole were reacted directly, ultimately producing a regiorandom polymer referred to in FIG. 1 as PRF. To synthesize the regioregular polymer (P2F), in which the fluorine atoms in alternating structural units point toward the same CDT unit, the symmetric monomer, M2 in FIG. 1, was first prepared by fine control of the Stille reaction temperature and the ratio of M1 and dibromide,[9a] then carried out the polymerization with M1 and M2. Polymer PDF, with difluorinated BT fragments, was obtained by the polymerization of M1 and 4,7-dibromo-5,6-difluorobenzo[2,1,3]thiadiazole. The molecular weight influence was also considered, particularly in view of subsequent comparisons of physical properties.[2d,5,12] The monomer ratio was varied and the Soxhlet extraction purification procedure was optimized by using different solvents. Synthetic details are provided in the Supporting Information (SI)[22]. These efforts provided molecular weights in the range of 50-70 kDa for each polymer.

b. Polymer Characterization

With these four polymers in hand, the UV-vis absorption, energy levels, OFET device performance, and film organization and morphologies were investigated with the goal of obtaining insight into the effect of fluorine substitution.

UV-vis absorption was used to examine optical transitions. Solution absorption measurements were carried out in chlorobenzene solvent. As shown in FIG. 2(a), the four polymers show peaks near 430 nm assigned to π-π* transitions. Peaks in the near-IR and IR regions are attributed to intramolecular charge transfer (ICT) excitations.[7] By examination of the absorption maxima and onsets, one observes that PBT is the most red-shifted chromophore, while the di-fluorinated polymer PDF is the most blue-shifted, see Table 1 for a summary of relevant data. The excitation profiles of the two mono-substituted polymers PRF and P2F lie between those of PBT and PDF and are almost identical to each other, with their maximum peaks at 780 nm and 782 nm, respectively.

TABLE 1

Summary of absorption characteristics and orbital energy levels.

| Polymer | $\lambda_{sol}$ (nm) | $\lambda_{film}$ (nm) | $Eg^{opt}$ (eV) | $E_{HOMO}$ (eV) | $E_{LUMO}$ (eV) |
|---|---|---|---|---|---|
| PBT | 436, 803 | 436, 793 | 1.25 | −4.80 | −3.55 |
| PRF | 431, 780 | 431, 778 | 1.27 | −5.05 | −3.78 |
| P2F | 432, 782 | 431, 781 | 1.25 | −5.03 | −3.78 |
| PDF | 427, 756 | 427, 755 | 1.30 | −5.19 | −3.89 |

$\lambda_{sol}$ and $\lambda_{film}$ refer to absorption peak values in chlorobenzene and in the thin film, respectively;
$Eg^{opt}$ is the optical band-gap determined by film absorption onset;
$E_{HOMO}$ and $E_{LUMO}$ are the energy levels from CV measurements and optical band-gaps.

Thin films were prepared by spin-casting from the corresponding chlorobenzene solution and the absorption spectra were measured. As shown in FIG. 2(b) and Table 1, the maxima of the ICT peaks remain largely unchanged, relative to solution. However, one observes a larger contribution from the low energy shoulder, leading to substantial differences in the absorption onsets. The optical band gaps are determined by corresponding thin film absorption onsets, which provide band-gaps of 1.25 eV, 1.27 eV, 1.25 eV and 1.30 eV for PBT, PRF, P2F and PDF respectively. It is interesting to note that the regiorandom (PRF) and regioregular (P2F) versions of the conjugated polymer containing F-BT are nearly identical. However, as demonstrated below, these two materials have very different charge transport characteristics.

Cyclic voltammetry was used to estimate HOMO energy levels by measuring the oxidation potential onsets.[13] As shown in Figure S3 in the SI[22], the HOMO level of PBT is −4.80 eV. After mono fluorine substitution, the HOMO levels decrease, with PRF and P2F displaying HOMO levels about −5.05 eV and −5.03 eV respectively. When two fluorine atoms are introduced to the BT unit, the HOMO level decreases further to −5.19 eV. These results highlight the influence of fluorine substitution, which reduces the HOMO levels by as much as 0.39 eV. From a practical perspective the lower HOMO value suggests that, among the polymers studied here, PDF should have the best air-stability in OFET applications.[8] Lowest unoccupied molecular orbital (LUMO) energy levels were calculated by adding the optical band-gaps to the HOMO levels. As shown in Table 1, the LUMO levels also decrease with increasing fluorine substitution, in agreement with the stronger electron deficient nature of FBT and DFBT units relative to BT. It is interesting to note that the stabilization of HOMO and LUMO levels by F substitution is similar, which may be surprising in view of the A units greater participation in determining the LUMO levels.[14]

Grazing-incidence wide-angle X-ray scattering (GIWAXS) was used to investigate thin film organization.[21] The 2D diffraction images are provided in the SI Figure S4-S7[22], and the line-cut profiles are shown in FIG. 2(c) and FIG. 2(d). In the out of plane direction, there is a strong peak around 0.25 Å$^{-1}$. A peak around 0.5 Å$^{-1}$ corresponding to the $2^{nd}$ order for all polymers, is assigned to alkyl chain stacking features. The alkyl chain stacking distances of all polymers are almost identical at about 2.4 nm, consistent in that they all contain similar hexyldecyl solubilizing unit and suggesting that all polymers share similar lattice organizations. There is no observable peak in the region of 1.0-2.0 Å$^{-1}$. In the in-plane direction, there is a strong peak around 1.8 Å$^{-1}$ for all polymers, which is assigned to π-π stacking.

Again, the π-π distances are nearly identical (0.35 nm). These features indicate that these polymers present edge-on orientation relative to the substrate plane and also indicate that fluorine substitution in this general backbone framework does not change the crystallite organizations under the film processing conditions disclosed here.

c. OFET Device Characterization

Bottom contact, bottom gate OFETs were fabricated using devices with the following architecture: polymer/Au/SAM/SiO$_2$/Si (doped). Decyltrichlorosilane (DTS) was used as the self-assembled monolayer on the silicon oxide substrate. Thin films were prepared via doctor-blading[15] and the complete details are provided in the SI[22]. Table 2 provides average and maximum mobilities, as determined under nitrogen inside a glovebox by examination of the saturation current regime, together with the corresponding on/off ratios. Average mobilities were calculated from 8 devices.

Typical output curves obtained with OFET devices are provided in FIGS. 3(a)-3(d). At high $V_g$ (−30−−60V), $I_{drain}$ is saturated when $V_{drain}$ is greater than −70 V. At lower $V_g$, one observes $I_{drain}$ increases with $V_{drain}$ in the range of −40 to −100 V. This feature suggests injection of electrons and therefore an ambipolar nature of the devices.[16] Comparison of FIG. 3(a) vs. 3(d) shows that when the hydrogen atoms are substituted with fluorine atoms, the ambipolar characteristics are more pronounced. One possible reason is that the lower LUMO levels are decreased as more fluorine substitutions have been introduced and that more electron-withdrawing groups can further stable the negative charges that electron transport would improve.[17] The transfer curves are shown in SI Figure S10[22]. The $I_{drain}^{1/2}$ vs. $V_g$ curves show nearly-ideal single slope characteristics.[18]

TABLE 2

Polymer OFET highest and average mobilities.

| Polymer | M$_n$ (kDa) | PDI | Mobility cm$^2$V$^{-1}$s$^{-1}$ | On/off | V$_{th}$ (V) |
|---|---|---|---|---|---|
| PBT | 68 | 3.6 | 1.4 (1.1 ± 0.1) | 6.3 × 10$^2$ | 10.1 |
| PRF | 53 | 3.3 | 0.4 (0.3) | 5.5 × 10 | 16.4 |
| P2F | 62 | 3.4 | 1.2 (0.9 ± 0.2) | 5.5 × 10 | 14.6 |
| PDF | 67 | 4.1 | 0.3 (0.3) | 2.8 × 10 | 9.6 |

Hole mobilities determined through measurements of OFETs containing different semiconductor polymers are summarized in Table 2. These data indicate that the polymer PBT, at least under these experimental conditions, shows a maximum mobility of 1.4 cm$^2$V$^{-1}$s$^{-1}$. The regiorandom polymer PRF obtains a maximum mobility of 0.4 cm$^2$V$^{-1}$s$^{-1}$, while its regioregular countpart P2F obtains a maximum mobility of 1.2 cm$^2$V$^{-1}$s$^{-1}$. The molecule weight (53 kDa) for the PRF is slightly lower than the other three polymers (60-70 kDa). To verify the molecule weight influence on the mobility, a higher molecular weight batch of PRF was synthesized having M$_n$ of 128 kDa and a PDI of 4.4. However, the higher molecule weight batch exhibits a maximum mobility of 0.3 cm$^2$V$^{-1}$s$^{-1}$ (See SI Table-S3[22]). Therefore, there seems to be no strong molecular weight influence on the performance for PRF at least within the range of the molecular weights investigated in these studies. When comparing PRF and P2F, which have similar chemical structures and absorption profiles, but differ with respect to the structural precision of the backbone, the regioregular polymer (avg. 0.9±0.2 cm$^2$V$^{-1}$s$^{-1}$) exhibits substantially improved performance than the regiorandom counterpart (avg. 0.3 cm$^2$V$^{-1}$s$^{-1}$). The di-fluorinated PDF obtains the lowest mobility, of about 0.3 cm$^2$V$^{-1}$s$^{-1}$ for both the maximum and average mobility. It is interesting since the fluorine substitution could enhance the packing and crystallinity, and in the past, DFBT has been widely reported as a better acceptor unit relative to the BT both in OFET and OPV devices,[19] but here seems not the case.[20]

Atomic force microscopy (AFM) was used to investigate the surface topographic features of devices, as a function of fluorine substitution. Height images are shown in the SI Figure S3[22]. There is no clear alignment in any of them in agreement with the result that their mobilities are not dependent on the blading direction. All films form continuous polymer domains. It seems there is no obvious difference in the film topography that could support the mobility difference in the device.

Figure 4:
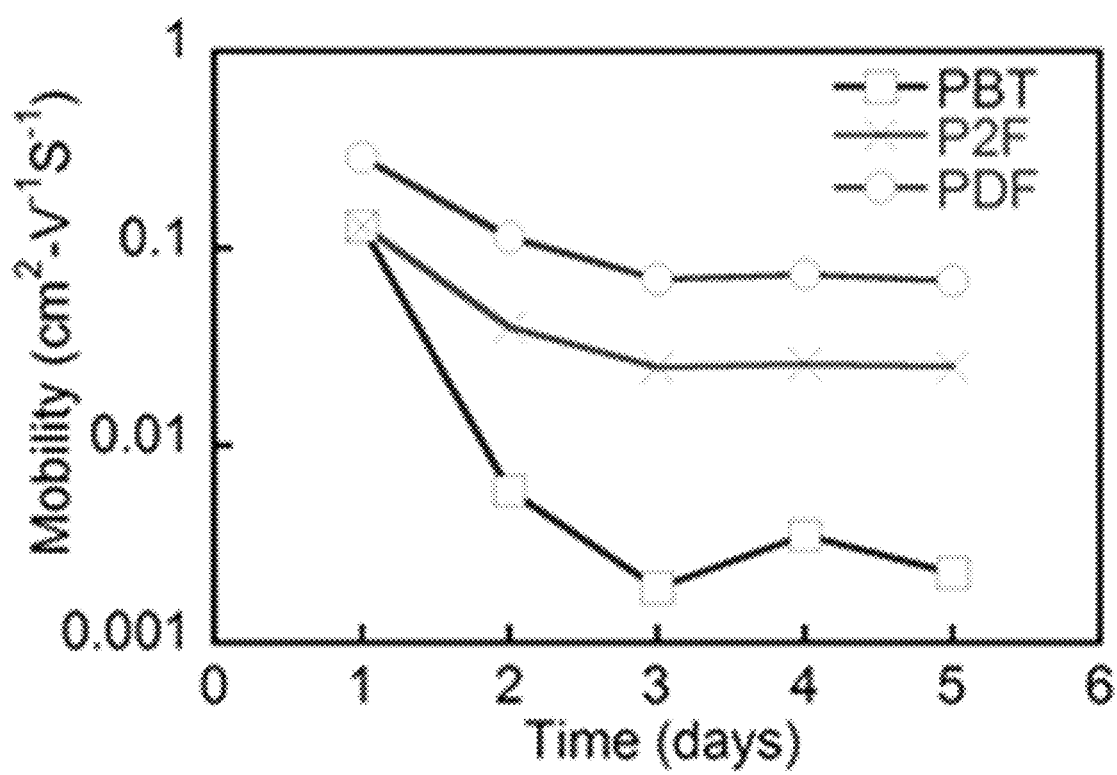
FIG. 4 plots polymer OFET mobilities tested in ambient condition, wherein the semiconducting polymers are non-aligned (or have no clear alignment as measured in a top surface of an AFM image of the semiconducting polymers) according to one or more embodiments of the present invention.

The air stability of PBT, P2F and PDF OFET devices were investigated to verify the benefit of lowering the HOMO levels as a function of fluorine substitutions. Their OFET device performance was measured in ambient conditions after exposure in air for one day and five days, respectively. Their transfer curves are provided in the SI Figure S11[22], and their mobilities as a function of time are shown in FIG. 4. It is very obvious that the device with PBT is very instable in the air as the mobility decreased to 0.002 cm$^2$V$^{-1}$s$^{-1}$ after 5 days, which is in agreement with the previous report.[5a] After 5 days, mobility of the mono-fluorinated polymer P2F decreased to 0.03 cm$^2$V$^{-1}$s$^{-1}$ and mobility of the di-fluorinated polymer PDF reduced to 0.07 cm$^2$V$^{-1}$s$^{-1}$. The higher mobility of PDF in air addressed the importance of low-lying HOMO level for OFET applications.

The above results show the present disclosure has developed three novel low band-gap polymers for OFET applications. Fluorine substitution was shown to significantly lower the energy levels. Regioregularity was once again demonstrated as an important design strategy since the mobility of P2F is improved when compared to PRF. However, there appears to be no influence of the molecular structure on the alkyl chain or π-π stacking distance. This is really a subtle feature. It is interesting that the regioregular mono-fluorinated P2F exhibits a similar mobility but the di-fluorinated PDF displayed a lower mobility relative to the non-fluorinated PBT polymer. Nevertheless, PDF exhibited superior advantages in the air stable OFET device applications relative to PBT and P2F as it displayed remarkably deeper HOMO levels.

Figure 5:
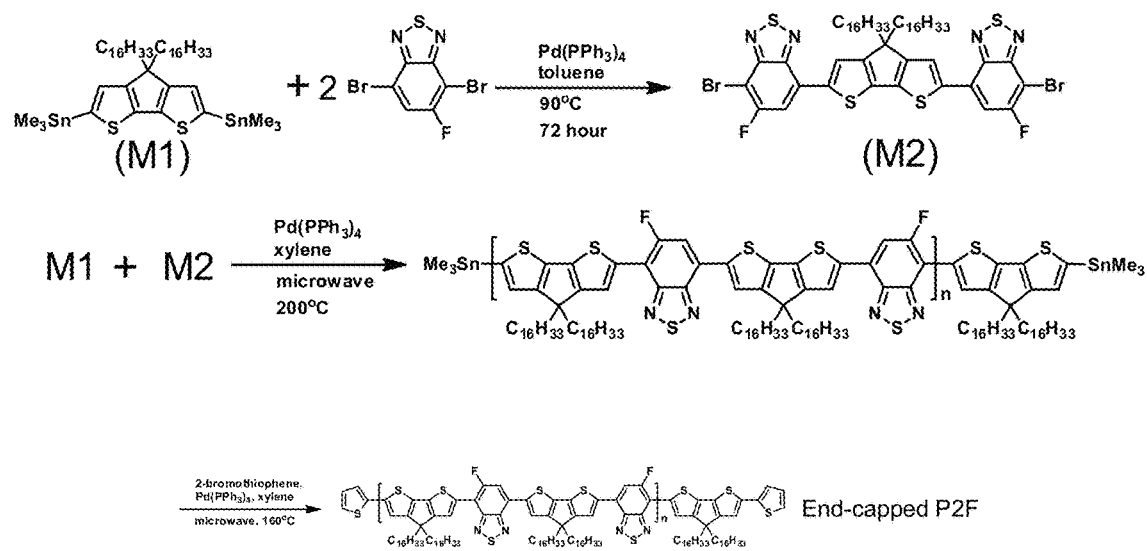
FIG. 5 illustrates a scheme for fabricating an end capped semiconducting polymer.

II. Second Embodiment: Investigation of P2F Properties as a Function of Synthesis Conditions a. P2F Synthesis with End Capping FIG. 5 illustrates a method of synthesizing P2F with end capping. The procedure is as follows.

M1 (100 mg, 0.105 mmol or 105 mg, 0.11 mmol or 110 mg, 0.115 mmol), M2 (109 mg, 0.1 mmol, synthesized according to the same procedure in P2 polymer synthesis[6, 2d]), Pd(PPh$_3$)$_4$ (6 mg, 0.005 mmol), and xylene (2 mL) were added to a 2-5 mL microwave tube in a nitrogen atmosphere glovebox. The tube was transferred out of the glove box, and subjected to the following reaction conditions in a microwave reactor: 80° C. for 2 minutes (min), 130° C. for 2 min, 160° C. for 2 min, and 200° C. for 40 min. The reaction was allowed to cool to room temperature, and then the vial was transferred back to the glovebox. The vial was opened to add Pd(PPh$_3$)$_4$ (3 mg), 2-bromothiophene (0.1 mL) and xylene (2 mL) for the end-capping reaction. Then the vial was sealed again, transferred out of the glove box and subjected to heating in the microwave reactor under the conditions of 80° C. for 2 min, 130° C. for 2 min, 160° C. for 20 min. The reaction was allowed to cool to room temperature and the resulting polymer was precipitated in methanol. The precipitates were collected by filter paper and extracted with methanol, dichloromethane and chloroform, respectively, via a Soxhlet extractor. The chloroform solution was concentrated under vacuum. Then, the concentrated polymer solution was purified to remove the catalyst residue (see section c. below). Then, the polymer was concentrated again and was added dropwise to methanol under the stirring. The polymer was precipitated, collected via filter paper, and dried over in the vacuum. The yield varied from 70% to 94% as a function of different M1/M2 ratios.

A very high M1 purity (>99%, or preferable >99.5% by $^1$H NMR) is achieved using carefully controlled anhydrous reaction conditions (including using anhydrous solvents and chemicals, thoroughly dried monomers, flame dried glassware, conducting the reaction under dry argon or nitrogen protection atmosphere or in a glove box). The high monomer purity is important for polymer quality and molecular weight control, although sometimes led to very high molecular weight and an insoluble polymer. Low monomer purity often led to low polymer molecular weight or oligomer formation and defects in polymer structure.

b. Impact of Monomer Ratio

As described in section a. above, the P2F was synthesized using different M1/M2 ratios (ratios of 1.05/1, 1.10/1 and 1.15/1). Surprisingly and unexpectedly, it was discovered that a slight excess amount of the M1 monomer during synthesis yielded superior control of the polymer molecular weight, high polymerization yield, and also led to a tin only end-functionalized intermediate polymer.

1. The ratio of 1.15/1 yielded P2F having a molecular weight of about $M_n$~50 kDa, which gave the best solubility and OFET performance combination.
2. The ratio of 1.10/1 yielded P2F having a molecular weight of about $M_n$~100 kDa. The solubility was much worse, but still soluble in hot chlorobenzene. The OFET performance was slightly lower as compared to the OFET comprising a 50 kDa batch polymer.
3. The ratio of 1.05/1 yielded an insoluble polymer, even in hot chlorobenzene (under reflux).
4. Since the amount of M1 was more than the amount of M2 in the polymerization, a tin end-functionalized intermediate polymer was formed and only one end-capping reaction (e.g. adding the 2-bromothiophene) was needed.
5. Polymer molecular weight can be controlled by controlling M1/M2 ratio below 1 (i.e., using an M1/M2 ratio of less than 1), except the intermediate polymer in this case is bromide end-functionalized and one end-capping reaction (e.g. using 2-trimethyltinthiophene) is needed.
6. High polymerization yield in a range from 70% to 94% was achieved using the above described monomer purity and ratio control.

Note: The relationship between monomer ratio and polymer molecular weight also depends on the monomer type, reactivity and purity. The relationship described above applies well to the above monomers having the above described purity. Adjustment may be needed when applying the methods described herein to other systems.

c. Catalyst Residue Removal

Various methods were used to remove the residue catalyst and tin in the crude polymer.

The concentrated polymer solution was divided into three portions so as to investigate different catalyst removal techniques.

(i) First Method:

The first portion was concentrated and added dropwise to methanol, and then the precipitate was collected and dried in a vacuum. This batch of polymer was named P2F-115. This method only removes some catalyst residue which is soluble in methanol.

(ii) Second Method:

The second portion was mixed with sodium diethyldithiocarbamate aqueous solution, heated at 50° C. and stirred for 3 hours (sodium diethyldithiocarbamate is a ligand to chelate residue metal ions, effective to remove Pd catalyst, and also remove some tin residue). The organic phase was then separated and washed with water three times. The organic phase was concentrated and added dropwise to methanol to precipitate the polymer. Then, the second batch was collected and dried in the vacuum and named P2F-115S.

(iii) Third Method:

The third portion was purified by passing the third portion through a short silica-gel column. The collected solution was then concentrated and added dropwise to methanol, and the precipitate was collected, dried in the vacuum and named P2F-115C. This method also removes some tin residue.

The Pd content (ppm, μg/g) in the polymer (coming from the catalyst Pd(PPh$_3$)$_4$ in the polymerization) was measured by ICP-MS.

TABLE 3

| Different batches | P2F-115 | P2F-115S | P2F-115C |
|---|---|---|---|
| Pd residue (ppm) | 2800 | 11 | 200 |

The results show the P2F polymer without catalyst removal treatment contained a high quantity of Pd residue. The results also show that both silica-gel column chromatography purification (second method) and sodium diethyldithiocarbamate treatment (third method) can significantly remove the Pd residue, but that the sodium diethyldithiocarbamate treatment is a superior method for Pd residue removal (i.e., treatment of P2F with sodium diethyldithiocarbamate removes more Pd residue). The two methods (sodium diethyldithiocarbamate treatment and silica-gel column chromatography purification) can also be combined for more effectiveness (increased Pd residue removal from the P2F). Both methods can be easily scaled up for the purification of a large quantity of polymers for industrial production.

Process Steps

Figure 6:
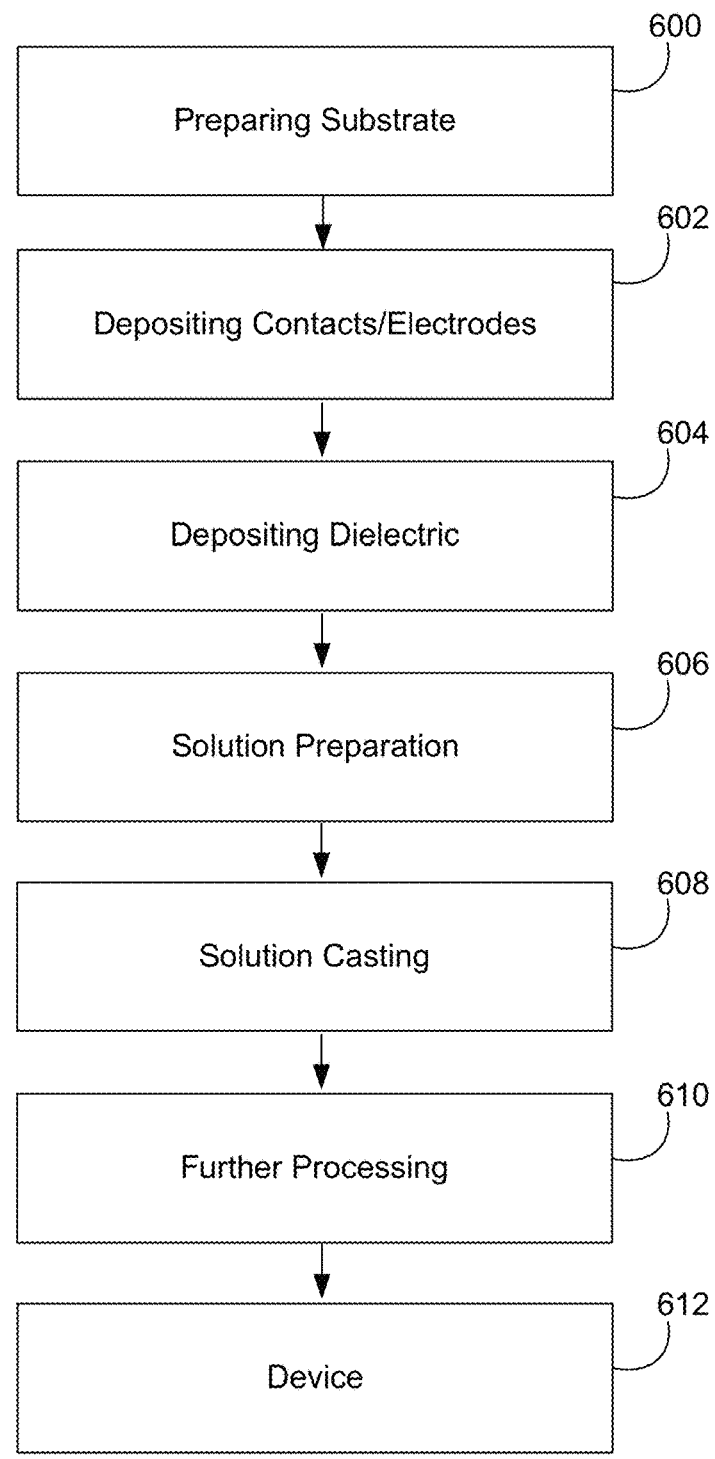
FIG. 6 is a flowchart illustrating a method of fabricating an OFET according to one or more embodiments of the invention.

FIG. 6 is a flowchart illustrating a method for fabricating an OFET. The method can comprise the following steps.

Block 600 represents obtaining/providing and/or preparing a substrate. In one or more embodiments, the substrate comprises a flexible substrate. Examples of a flexible substrate include, but are not limited to, a plastic substrate, a polymer substrate, a metal substrate, or a glass substrate. In one or more embodiments, the flexible substrate is at least one film or foil selected from a polyimide film, a polyether ether ketone (PEEK) film, a polyethylene terephthalate (PET) film, a polyethylene naphthalate (PEN) film, a polytetrafluoroethylene (PTFE) film, a polyester film, a metal foil, a flexible glass film, and a hybrid glass film.

Block 602 represents optionally forming/depositing contacts or electrodes (e.g., p-type, n-type contacts, or a gate, source, and/or drain contacts) on or above (or as part of) the substrate.

In an OFET embodiment comprising a top gate and bottom contact geometry, source and drain contacts are deposited on the substrate. Examples of the source and drain contacts include, but are not limited to, gold, silver, silver oxide, nickel, nickel oxide (NiOx), molybdenum, and/or molybdenum oxide. In one or more embodiments, the source and drain contacts of the OFET further comprise a metal oxide electron blocking layer, wherein the metal includes, but is not limited to nickel, silver or molybdenum.

In an OFET embodiment comprising a bottom gate geometry, a gate electrode is deposited on the substrate. In one or more embodiments, the gate contact (gate electrode) is a thin metal layer. Examples of the metal layer for the gate include, but are not limited to, an aluminum layer, a copper layer, a silver layer, a silver paste layer, a gold layer or a Ni/Au bilayer. Examples of the gate contact further include, but are not limited to, a thin Indium Tin Oxide (ITO) layer, a thin fluorine doped tin oxide (FTO) layer, a thin graphene layer, a thin graphite layer, or a thin PEDOT:PSS layer. In one or more embodiments, the thickness of the gate electrode is adjusted (e.g., made sufficiently thin) depending on the flexibility requirement.

The gate, source, and drain contacts can be printed, thermal evaporated, or sputtered.

Block 604 represents optionally depositing a dielectric on the gate electrode, e.g., when fabricating an OFET in a bottom gate configuration. In this example, the dielectric is deposited on the gate contact's surface to form a gate dielectric.

The step can comprise forming a coating (e.g., a dielectric coating) or one or more dielectric layers, on the substrate. The dielectric layers can comprise silicon dioxide, a polymer (e.g., PVP) dielectric layer, a polymerized ionic liquid (PIL), or multiple dielectric layers (e.g., a bilayer dielectric). The dielectric layers can be solution coated on the substrate. A single polymer dielectric layer may be preferred in some embodiments (for easier processing, more flexibility). In one embodiment, the dielectric layers can form a polymer/SiO$_2$ bilayer. In another embodiment, the dielectric layers form a polymer dielectric/SiO$_2$/SAM multilayer with the SiO$_2$ on the polymer and the alkylsilane or arylsilane Self Assembled Monolayer (SAM) layer on the SiO$_2$. In another embodiment, the dielectric layers form a SiO$_2$/SAM bilayer with the alkylsilane or arylsilane SAM layer on the SiO$_2$. Various functional groups may be attached to the end of the alkyl groups to modify the surface property of the SAM layer.

The thickness of the coating/dielectric (e.g., SiO$_2$) may be adjusted/selected. For example, the thickness may be adjusted (e.g., made sufficiently thin) depending on the composition of the dielectric layers and the flexibility requirement. For example, in one embodiment, the dielectric layer might not include a polymer dielectric layer and still be flexible.

Block 606 represents fabricating or obtaining one or more semiconducting polymers.

In one or more embodiments, each of the semiconducting polymers comprise polymer chains having a backbone comprising an aromatic ring, the aromatic ring comprising an element (e.g., fluoro functionality) having reduced susceptibility to oxidization as compared to nitrogen.

In one or more embodiments, the semiconducting polymers have fluoro functionality comprising an acceptor structure including a regioregular fluoro-phenyl unit.

In one or more embodiments, the semiconducting polymer comprises a (e.g., regioregular) conjugated main chain section, the conjugated main chain section having a repeat unit that comprises a compound of the structure:

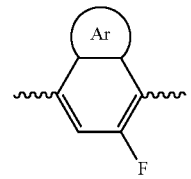

wherein Ar is a substituted or non-substituted aromatic functional group, or Ar is nothing and the valence of the ring comprising fluorine (F) is completed with hydrogen. In one or more embodiments, the ring comprising F is regioregularly arranged along the conjugated main chain section.

In one or more examples, the ring comprising the F has the structure:

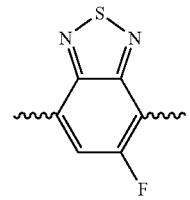

Figure 7A:
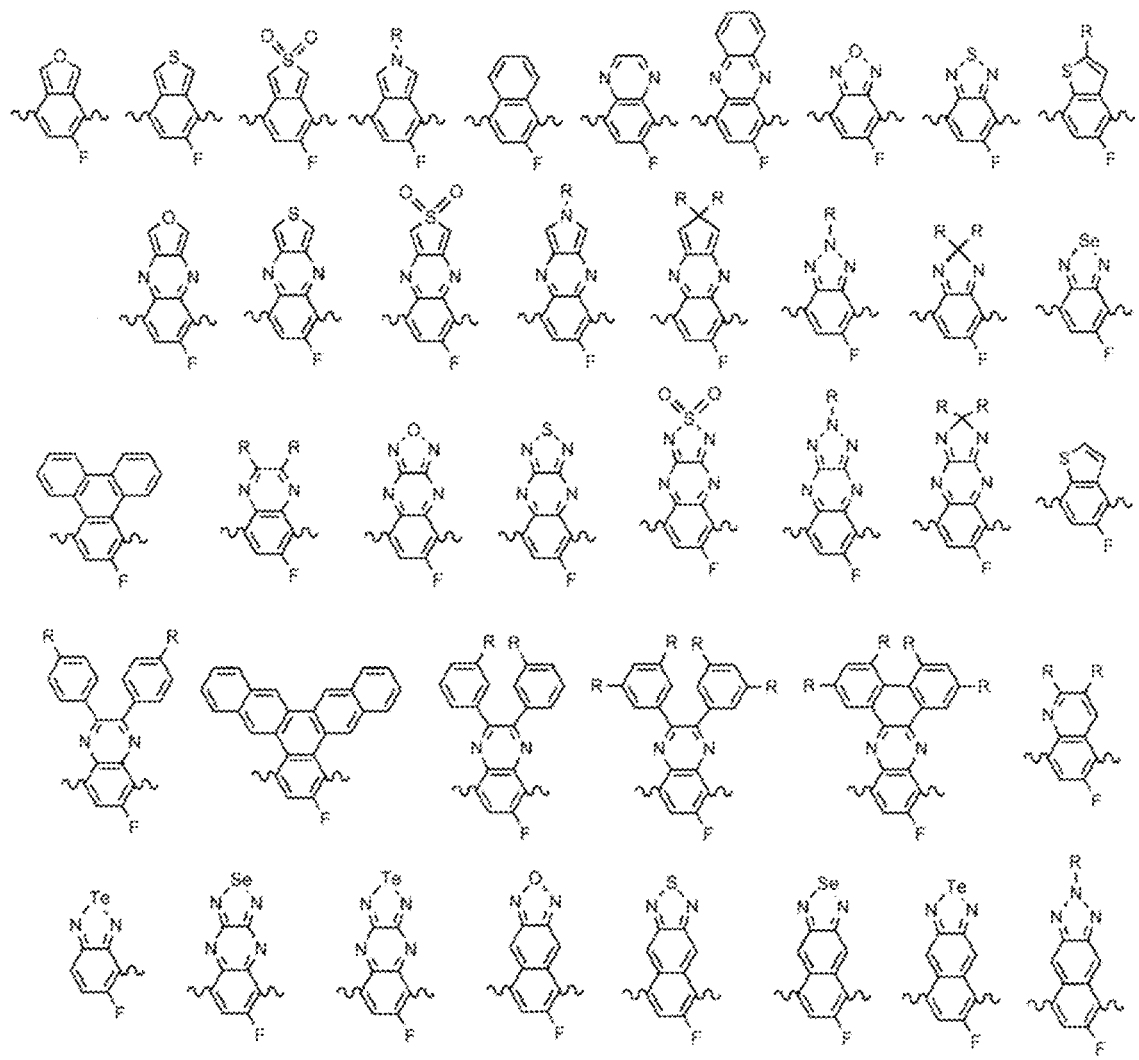
FIG. 7a illustrates examples for the ring unit comprising Fluorine in the semiconducting polymer, according to one or more embodiments of the present invention.

Other examples include those illustrated in FIG. 7a, where each R is independently a substituted or non-substituted alkyl chain, which can be a $C_6$-$C_{30}$ substituted or non-substituted alkyl chain, —(CH$_2$CH$_2$O)n (n=2~20), $C_6H_5$, —$C_nF_{(2n+1)}$ (n=2~20), —(CH$_2$)$_n$N(CH$_3$)$_3$Br (n=2~20), —(CH$_2$)$_n$N(C$_2$H$_5$)$_2$ (n=2~20), 2-ethylhexyl, PhC$_m$H$_{2m+1}$ (m=1-20), —(CH$_2$)$_n$Si(C$_m$H$_{2m+1}$)$_3$ (m, n=1 to 20), $C_{12}H_{25}$, $C_{14}H_{29}$, $C_{16}H_{33}$, $C_{18}H_{37}$, or —(CH$_2$)$_n$Si(OSi(C$_m$H$_{2m+1}$)$_3$)$_x$(C$_p$H$_{2p+1}$)$_y$ (m, n, p=1 to 20, x+y=3), for example; in some embodiments, the R groups can be the same.

In one or more embodiments, the repeat unit further comprises a dithiophene of the structure:

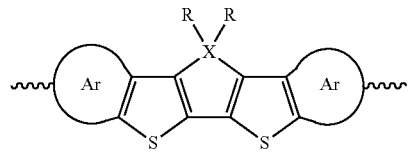

wherein each Ar is independently a substituted or non-substituted aromatic functional group, or each Ar is independently nothing and the valence of its respective thiophene ring is completed with hydrogen, each R is independently hydrogen or a substituted or non-substituted alkyl, aryl, or alkoxy chain, and X is C, Si, Ge, N or P. In some embodiments, the R groups can be the same. In the dithiophene, the R comprising the substituted or non-substituted alkyl, aryl or alkoxy chain can be a $C_6$-$C_{30}$ substituted or non-substituted alkyl or alkoxy chain, —(CH$_2$CH$_2$O)$_n$ (n=2~20), $C_6H_5$, —$C_nF_{(2n+1)}$ (n=2~20), —(CH$_2$)$_n$N(CH$_3$)$_3$Br (n=2~20), 2-ethylhexyl, PhC$_m$H$_{2m+1}$ (m=1-20), —(CH$_2$)$_n$N(C$_2$H$_5$)$_2$ (n=2~20), —(CH$_2$)$_n$Si(C$_m$H$_{2m+1}$)$_3$ (m, n=1 to 20), $C_{12}H_{25}$, $C_{14}H_{29}$, $C_{16}H_{33}$, $C_{18}H_{37}$ or —(CH$_2$)$_n$Si(OSi(C$_m$H$_{2m+1}$)$_3$)$_x$(C$_p$H$_{2p+1}$)$_y$ (m, n, p=1 to 20, x+y=3).

Figure 7B:
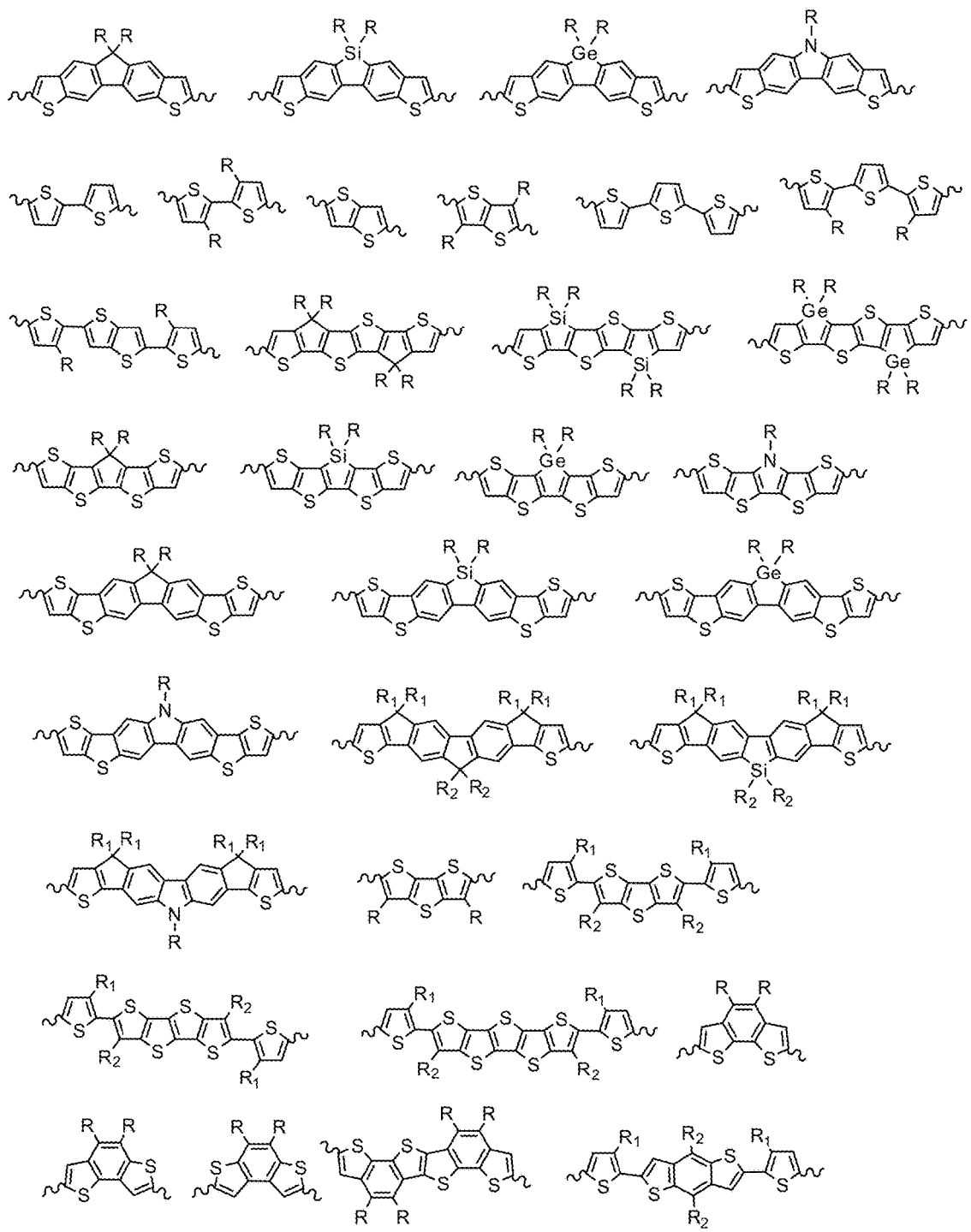
FIGS. 7b-7d illustrate examples for the dithiophene unit in the semiconducting polymers according to one or more embodiments of the present invention.
Figure 7C:
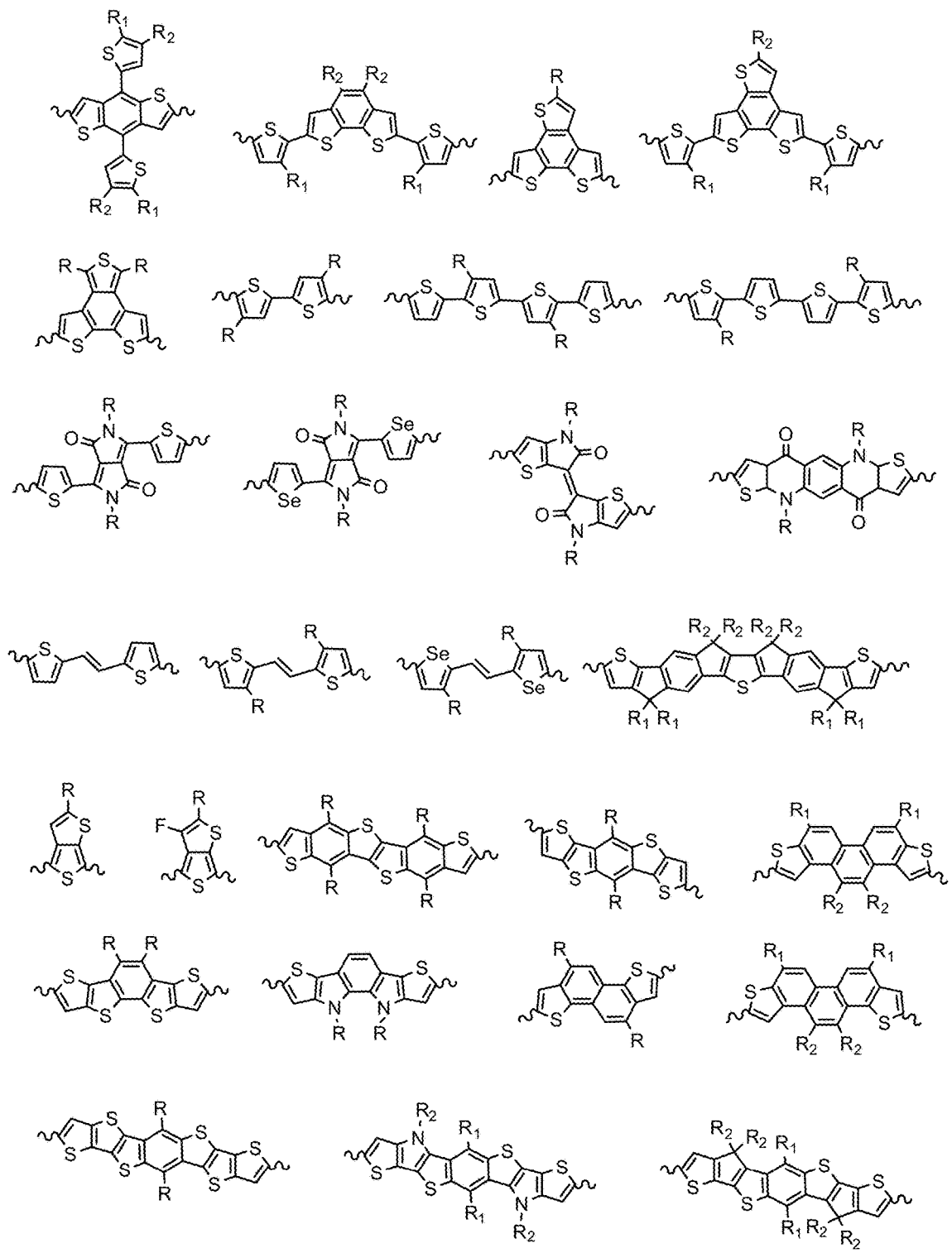
Figure 7D:
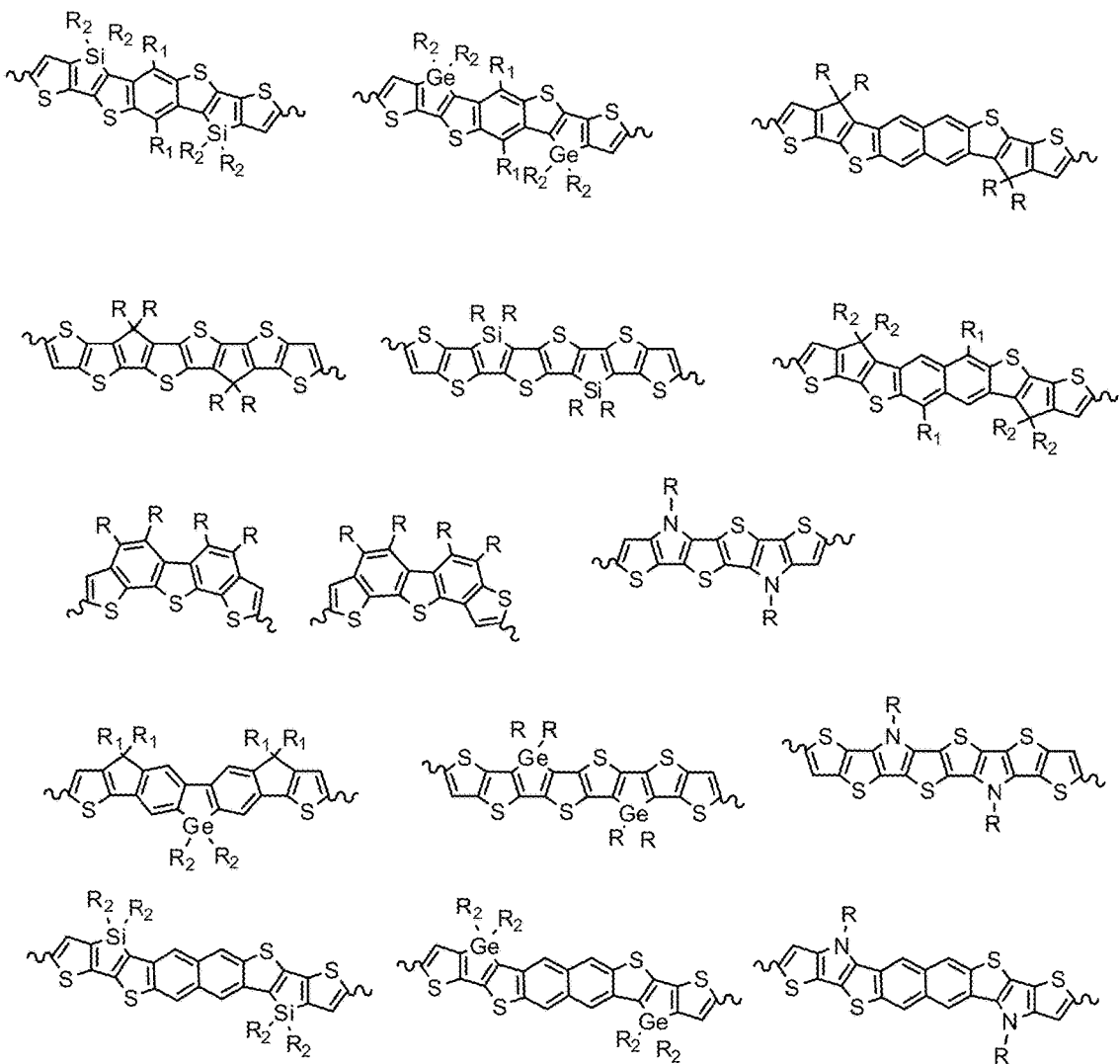

Examples of dithiophene units include those illustrated in FIGS. 7b-7d of the present disclosure and Table B (FIG.

30B) in U.S. Utility patent application Ser. No. 14/426,467, filed on Mar. 6, 2015, by Hsing-Rong Tseng, Lei Ying, Ben B. Y. Hsu, Christopher J. Takacs, and Guillermo C. Bazan, entitled "FIELD-EFFECT TRANSISTORS BASED ON MACROSCOPICALLY ORIENTED POLYMERS,", wherein the definition of R, R1 and R2 in FIGS. 7b-7d is the same as the definition for the R groups given above for FIG. 7a.

In one or more examples, the dithiophene unit comprises:

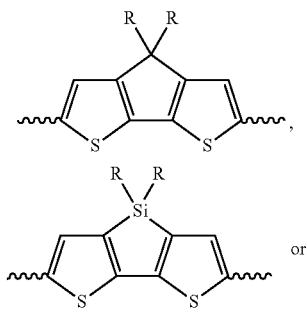

or

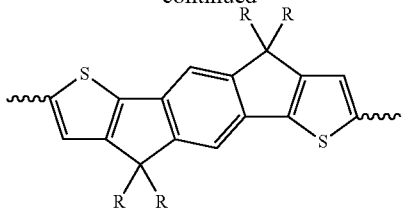

In one or more embodiments, the semiconducting polymer has the structure with repeating units D comprising the dithiophene and repeating units A comprising the ring comprising the fluorine, e.g., $[D-A-D-A]_n$ where n is an integer representing the number of repeating units, D is a donor structure, and A is an acceptor structure. In one or more embodiments, the structure has a regioregular conjugated main chain section having 5-150, or more, contiguous repeat units. In some embodiments, the number of repeat units is in the range of 10-40 repeats. The regioregularity of the conjugated main chain section can be 95% or greater, for example.

Thus, in one or more embodiments, the semiconducting polymer is a regioregular semiconducting polymer comprising a repeating unit of the structure:

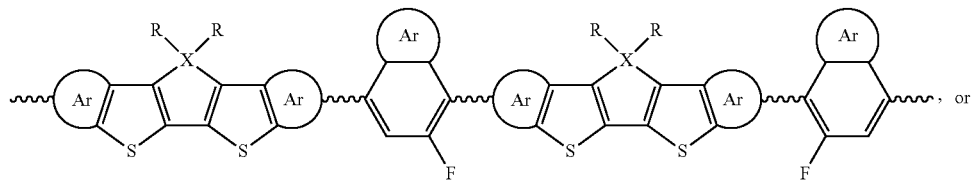, or

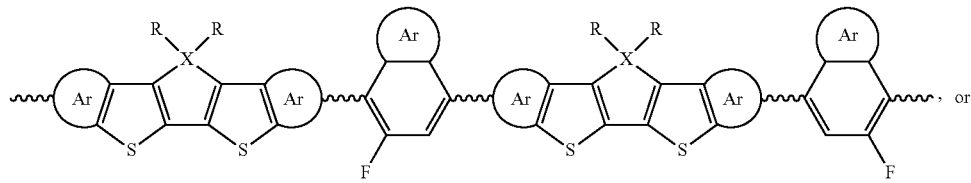, or

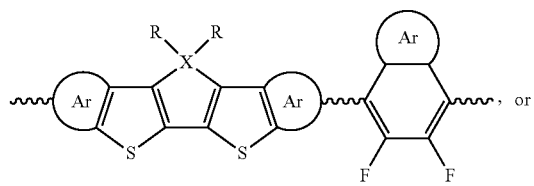, or

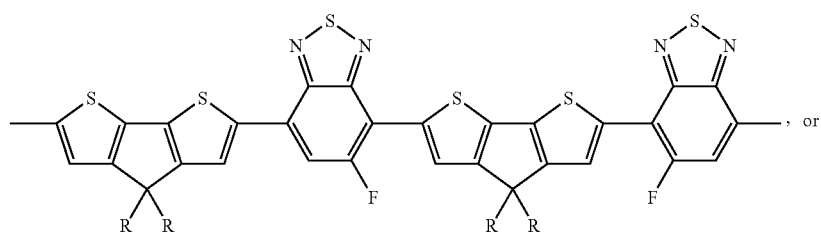, or

-continued

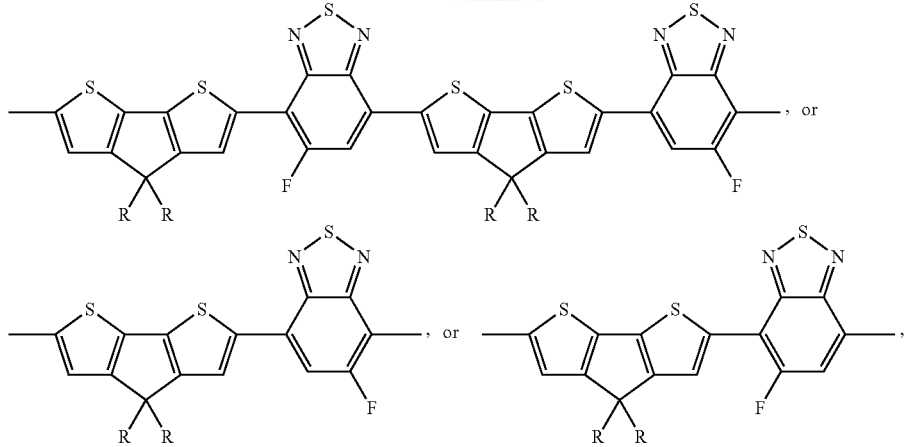

where the ring comprising F is regioregularly arranged along the conjugated main chain section pointing toward the direction shown in the structures above, Ar is a substituted or non-substituted aromatic functional group containing one, two, three or more aromatic rings, or Ar is nothing and the valence of the ring comprising fluorine (F) is completed with hydrogen, the R groups comprising the substituted or non-substituted alkyl, aryl or alkoxy chain can be a $C_6$-$C_{30}$ substituted or non-substituted alkyl or alkoxy chain, —$(CH_2CH_2O)n$ (n=2~20), $C_6H_5$, —$C_nF_{(2n+1)}$ (n=2~20), —$(CH_2)_nN(CH_3)_3Br$ (n=2~20), 2-ethylhexyl, $PhC_mH_{2m+1}$ (m=1-20), —$(CH_2)_nN(C_2H_5)_2$ (n=2~20), —$(CH_2)_nSi(C_mH_{2m+1})_3$ (m, n=1 to 20), $C_{12}H_{25}$, $C_{14}H_{29}$, $C_{16}H_{33}$, $C_{18}H_{37}$, or —$(CH_2)_nSi(OSi(C_mH_{2m+1})_3)_x(C_pH_{2p+1})_y$ (m, n, p=1 to 20, x+y=3).

For example, the semiconducting polymer can be regioregular poly[5-fluoro-[2,1,3]benzothiadiazole-4,7-diyl(4,4-dihexadecyl-4H-cyclopenta[2,1-b:3,4-b']dithiophene-2,6-diyl)-5-fluoro-[2,1,3]benzothiadiazole-7,4-diyl(4,4-dihexadecyl-4H-cyclopenta[2,1-b:3,4-b']dithiophene-2,6-diyl)] (P2F, also called PCDTFBT).

Further additives or compositions may be added to the solution, e.g., to form a blend.

Figure 8:
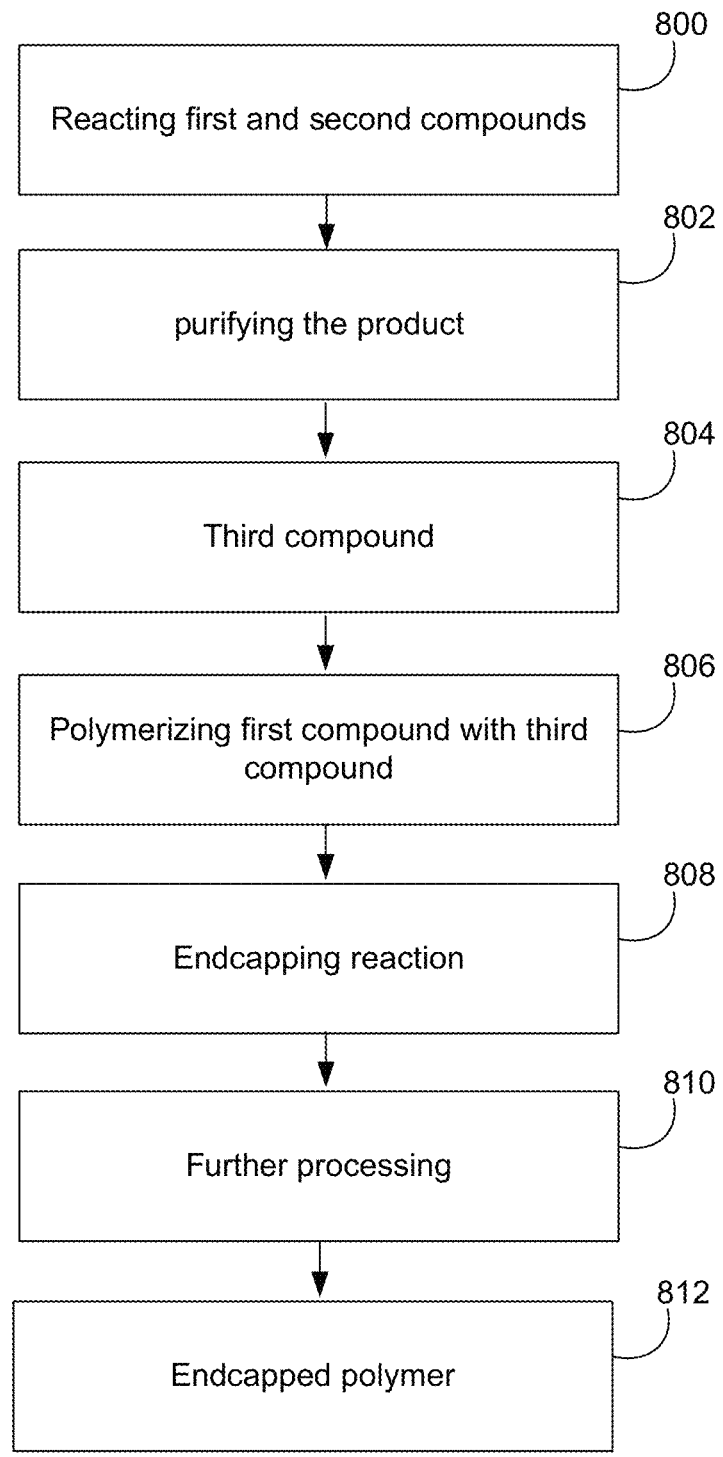
FIG. 8 illustrates a method of fabricating semiconducting polymers according to one or more embodiments of the present invention.

FIG. 8 is a flowchart illustrating a method of preparing the semiconducting polymers.

Block 800 represents performing a coupling reaction wherein a first compound and a second compound are coupled in a solution so as to form a product.

Examples of the first compound include, but are not limited to, a dithiophene or a compound having the structure (e.g., M1):

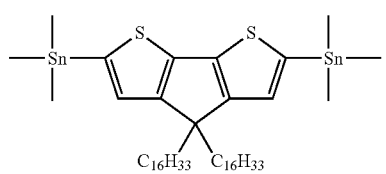

In one or more examples of the above structure, the $C_{16}H_{33}$ are replaced with R as described herein to achieve the desired R in the semiconducting polymers and/or the Sn is not required (e.g., the first compound is terminated with a proton on either side).

Examples of the second compound include, but are not limited to, a compound having the structure (Br-FBT-Br):

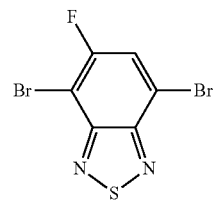

In one or more embodiments, the coupling reaction comprises mixing a solution comprising the first compound and the second compound to form a mixture and heating the mixture (e.g., to 90° C.) in an oil bath, obtaining the product.

Temperature and reactant ratio are controlled during the coupling reaction. In one or more examples, the coupling reaction coupling the first compound (M1) and the second compound (Br-FBT-Br) is conducted at a temperature between 50° C. to 130° C., preferably between 70° C. to 110° C., and more preferably at 90° C.

In various further examples, performing the coupling reaction comprises reacting an excess amount of the second compound as compared to the first compound so as to form the product. In one or more examples, the second compound (Br-FBT-Br) to M1 (Sn-CDT-Sn) ratio is between 1.5-4:1, but is preferably between 2-3:1 and more preferably between 2.2-2.5:1.

The use of the above described controlled temperature and ranges for the ratios of Br-FBT-Br to M1 were surprisingly and unexpectedly found to increase the yield of the third compound (M2) to at least 60%, e.g., in a range of 60%-70%. This is also a more effective utilization of the more expensive M1 compound, which is the limiting reactant here. For comparison, when a ratio of IT0312 to M1 of 2:1 and temperature of refluxing toluene was used for the coupling reaction, the yield of the resulting M2 analog monomer (IT1089) is only 44% [24]. Note that IT1089 used in [24] has a different structure as compared to M2 described herein: in IT1089, the fluorines point inwards, in comparison to M2 used in embodiments described herein where the fluorines point outwards.

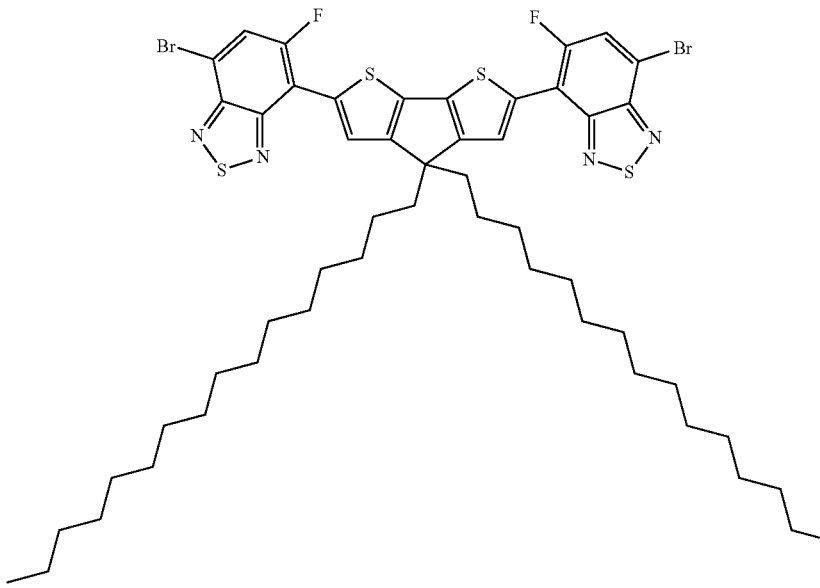

Block 802 represents purifying the product (e.g., in a solvent mixture, e.g., using chromatography). Examples of solvent mixtures include chloroform:hexane with more hexane than chloroform, e.g., 20%-33% chloroform, In one or more examples, the chloroform/hexane v/v ratio is ¼, ⅓, or, ½, or between ¼ and ½. Surprisingly and unexpectedly, it was discovered that selection of the proper solvent mixture (more hexane than chloroform) obtained the third compound (this is unexpected/surprising because a solvent comprising less hexane than chloroform (e.g., hexane:chloroform ratio of 1:3) is used during purification to obtain PCDTPT polymers.

Block 804 represents the end result of steps 800-802, a third compound.

In one or more embodiments, the third compound has the structure:

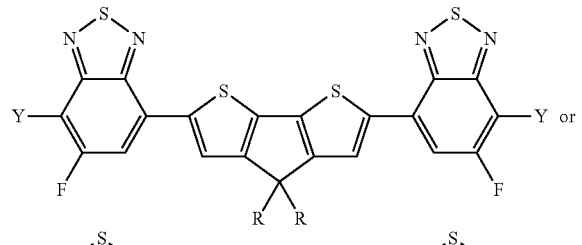

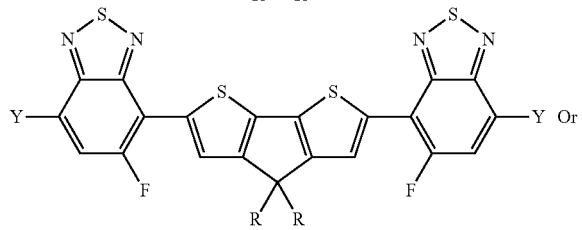

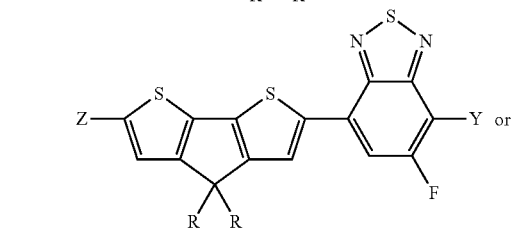

-continued

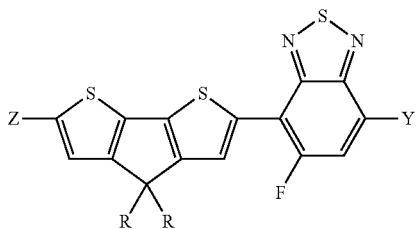

where each Y is bromide, iodide, pseudo-halides or triflate; Z is hydrogen, alkenyl, borate, Sn(Me)$_3$ or Sn(Bu)$_3$; each R is independently hydrogen or a substituted or non-substituted alkyl, aryl, or alkoxy chain.

In one or more embodiments, the third compound has the structure:

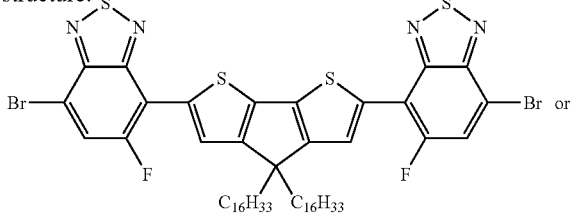

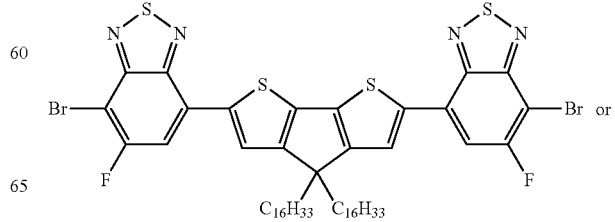

-continued

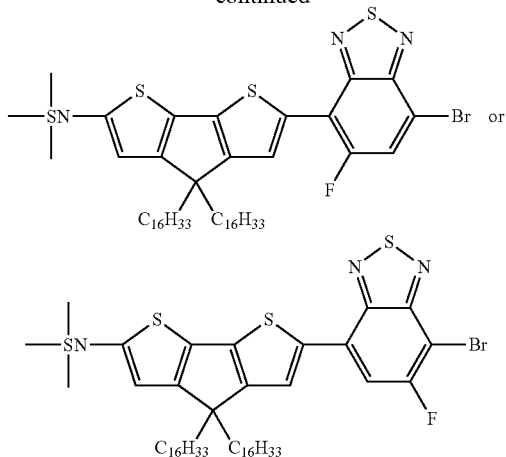

wherein, in one or more embodiments, $C_{16}H_{33}$ is replaced by R as described herein.

Block 806 represents polymerizing the first compound and the third compound in a polymerization reaction to obtain the regioregular semiconducting polymers described above in Block 606.

In a chemical reaction or polymerization, the reaction yield or polymerization yield is the amount of product obtained in the reaction. The reaction yield or polymerization yield can be given as the absolute yield (weight in grams or in moles) or percentage yield (a percentage without unit). The percentage yield is a measure of the effectiveness of a synthetic procedure, is calculated by dividing the amount of the obtained desired product by the theoretical yield (the unit of measure for both must be the same):

$$\text{percent yield} = \frac{\text{actual yield}}{\text{theoretical yield}} \times 100\%$$

The theoretical yield is the amount predicted by a stoichiometric calculation based on the number of moles of all reactants present. This calculation assumes that only one reaction occurs and that the limiting reactant reacts completely.

Block 808 represents performing an end capping reaction (e.g., in a presence of a catalyst such as palladium). In one or more examples, the step comprises reacting the semiconducting polymer intermediate (FIG. 5) with an aromatic bromide (e.g., 1-bromobenzene or 2-bromothiophene) or an aromatic tin (e.g., 2-trimethyltinthiophene) (e.g., in the presence of the catalyst) so as to obtain an end capped polymer.

The same polymerization reactions for conducting polymer synthesis (e.g., Stille coupling, Heck coupling, Suzuki coupling etc.) can be generally used for the end-capping.

In one or more examples, only one end-capping reagent, either an aromatic bromide (e.g., bromobenzene or bromothiophene) or an aromatic tin (e.g., trimethyltinthiophene), not both, was used in the end-capping reaction. the aromatic bromide is bromobenzene or bromothiophene.

Block 810 represents optional further processing.

In one or more examples, the step comprises treating and or purifying the end capped polymer so as to remove at least some of the catalyst and/or reduce at least some residual tin from the end capped polymer.

In one example, the step comprises combining the end capped polymer from Block 808 in solution with sodium diethyldithiocarbamate aqueous solution so as to form a mixture; heating the mixture; separating an organic phase from the mixture; washing the organic phase; concentrating the organic phase; and adding the organic phase drop wise to a solvent so as to precipitate a purified form of the end capped polymer.

In another example, the step comprises passing the end capped polymer of Block 808 in solution through a purification (e.g., silica gel) column so as to obtain a purified solution; and adding the purified solution drop wise to a solvent so as to precipitate a purified form of the end capped polymer.

The step may further comprise using purification or extraction techniques so that a polymer having a molecular weight in a range of 30-80 kDa can be extracted. Examples include extracting the polymerization product of Block 806 or the end capped product of Block 808 through a sequence of solvents (e.g., chloroform, hexane, acetone) to eliminate oligomers and large insoluble polymer as well as low molecular weight products. In one or more examples, the semiconducting polymer has a molecular weight in a range of 50 kDa or in a range of 30-80 kDa or 45-55 kDa.

In one or more embodiments, the semiconducting polymer has a molecular weight that is sufficiently small so that the semiconducting polymer is soluble in a solvent and solution processable, and sufficiently large so that an OFET comprising a channel including the polymer has a hole and/or electron mobility of at least 1.2 $cm^2V^{-1}s^{-1}$ in a saturation regime.

Block 812 represents the end result, an end capped semiconducting polymer and/or purified form of the end-capped semiconducting polymer.

In one or more examples, the end capped polymer has the following structure:

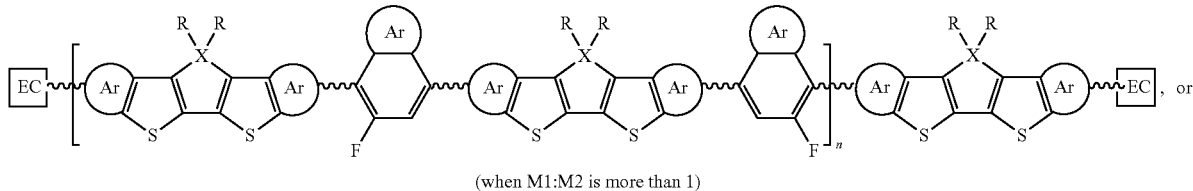

(when M1:M2 is more than 1)

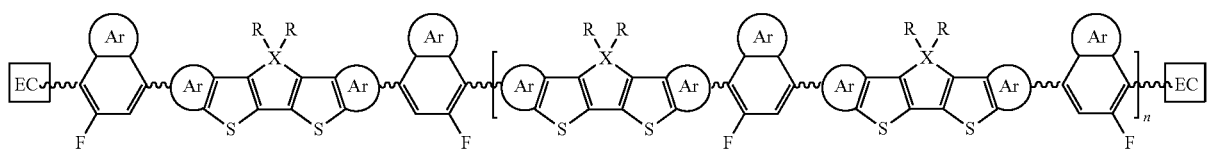

and wherein Ar and R are as disclosed above in Block 606 and EC is an end capping molecule or moiety (e.g., an aromatic moiety as described herein).

As described herein, the P2F was synthesized using different M1/M2 ratios (ratios of 1.05/1, 1.10/1 and 1.15/1). Surprisingly and unexpectedly, it was discovered that a slight excess amount of the M1 monomer yielded superior control of not only the polymer molecular weight, but resulted also in high polymerization percentage yield. For example, P2F polymer synthesis following the methods described herein and using M1 (110 mg, 0.115 mmol), M2 (109 mg, 0.10 mmol), $Pd(PPh_3)_4$ (6 mg, 0.005 mmol) yielded a purified P2F polymer of 140 mg, a percentage yield of 90%.

For comparison, when a monomer ratio of M1 (1.75 g, 1.84 mmol) to IT1089 (2 g, 1.84 mmol) of 1:1 was used for the polymerization reaction, the yield of the resulting purified polymer 1MP2 (P2F) is only 0.7 g (a percentage yield of 24%) [24], wherein IT1089 has the structure provided above. The reduced yield in [24] is likely due to the formation of high molecular weight, insoluble polymer as demonstrated above.

Thus, in various examples, the excess amount and a temperature at which the coupling reaction is performed (Block 800) and/or the ratio of M1/M2 during polymerization are such that a yield of the polymer is at least 70% or at least 80% (or in a range of 70%-94%).

In one or more examples, the end capped semiconducting polymer has a catalyst moiety content (e.g., palladium content) of less than 3000 parts per million (ppm), less than 200 ppm, or less than 10 ppm (e.g., in a range of 1-200 ppm).

The end capping groups EC can be any end capping group used in polymer synthesis, which convert/terminate reactive, unstable polymer end functionalities to stable chain ends. Examples of EC include an aromatic group including, but not limited to, the following structures:

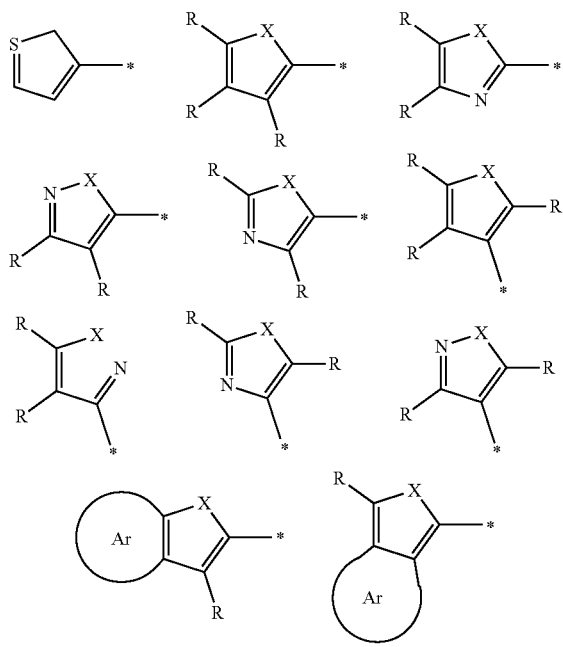

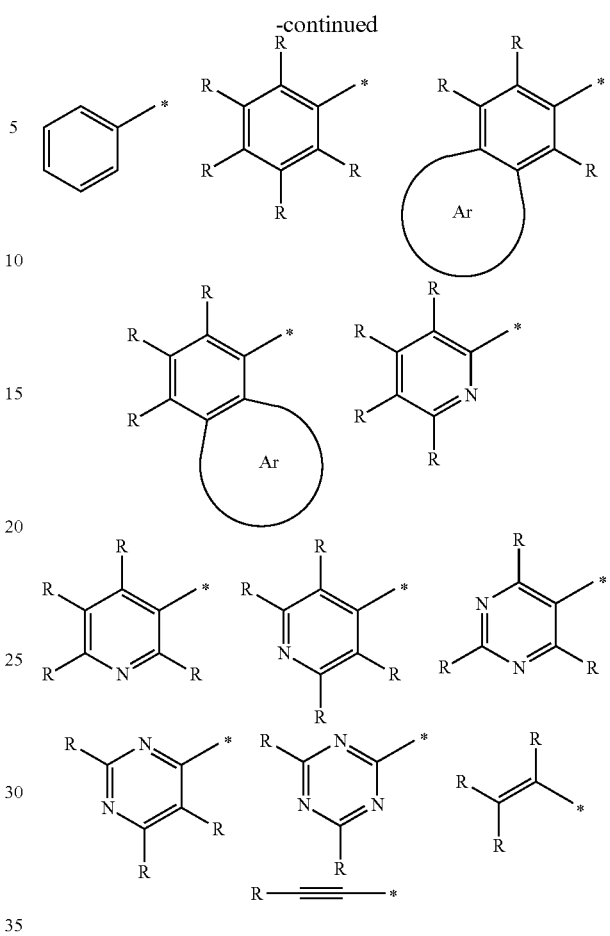

wherein each Ar is independently a substituted or non-substituted aromatic functional group, or each Ar is independently nothing and the valence of its respective ring is completed with hydrogen, each R is independently hydrogen, fluorine, chlorine, or a substituted or non-substituted alkyl, aryl, alkoxy, silyl, or amino chain; and X is $CR_2$, $SiR_2$, $GeR_2$, O, S, Se, NR, PR.

Block 608 represents solution casting/processing the solution comprising the semiconducting polymers, such that the semiconducting polymers are deposited in a film on or above the substrate or on the dielectric.

Solution casting methods include, but are not limited to, inkjet printing, bar coating, spin coating, blade coating, spray coating, roll coating, dip coating, free span coating, dye coating, screen printing, and drop casting.

Block 610 represents further processing the polymer film cast on the dielectric/substrate. The step can comprise annealing/curing/drying the polymer (or allowing the polymer to dry). The step can comprise depositing source and drain contacts, if necessary.

Figure 9:
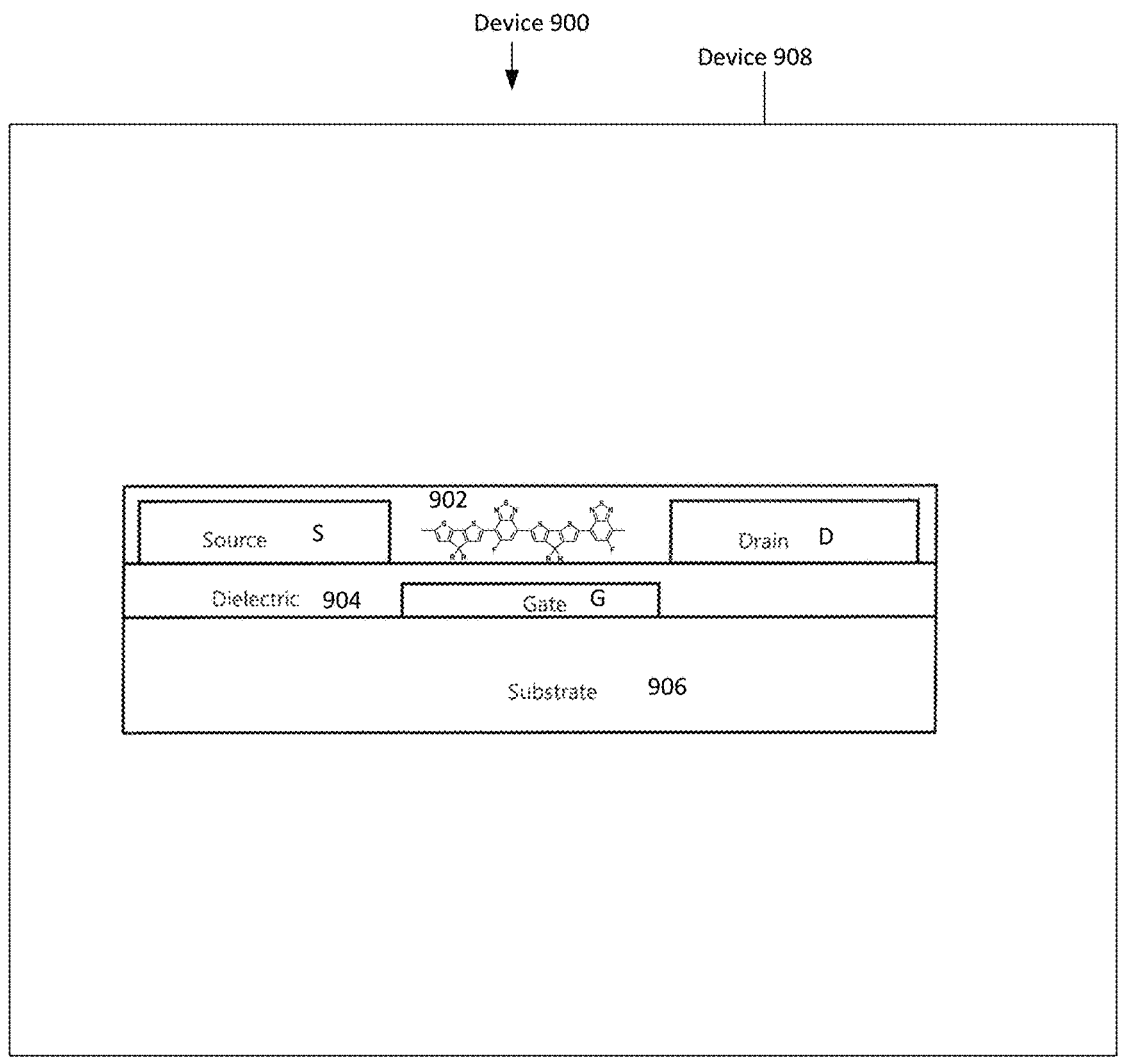
FIG. 9 illustrates a device comprising one or more OFETs according to one or more embodiments of the invention.
Figure 10:
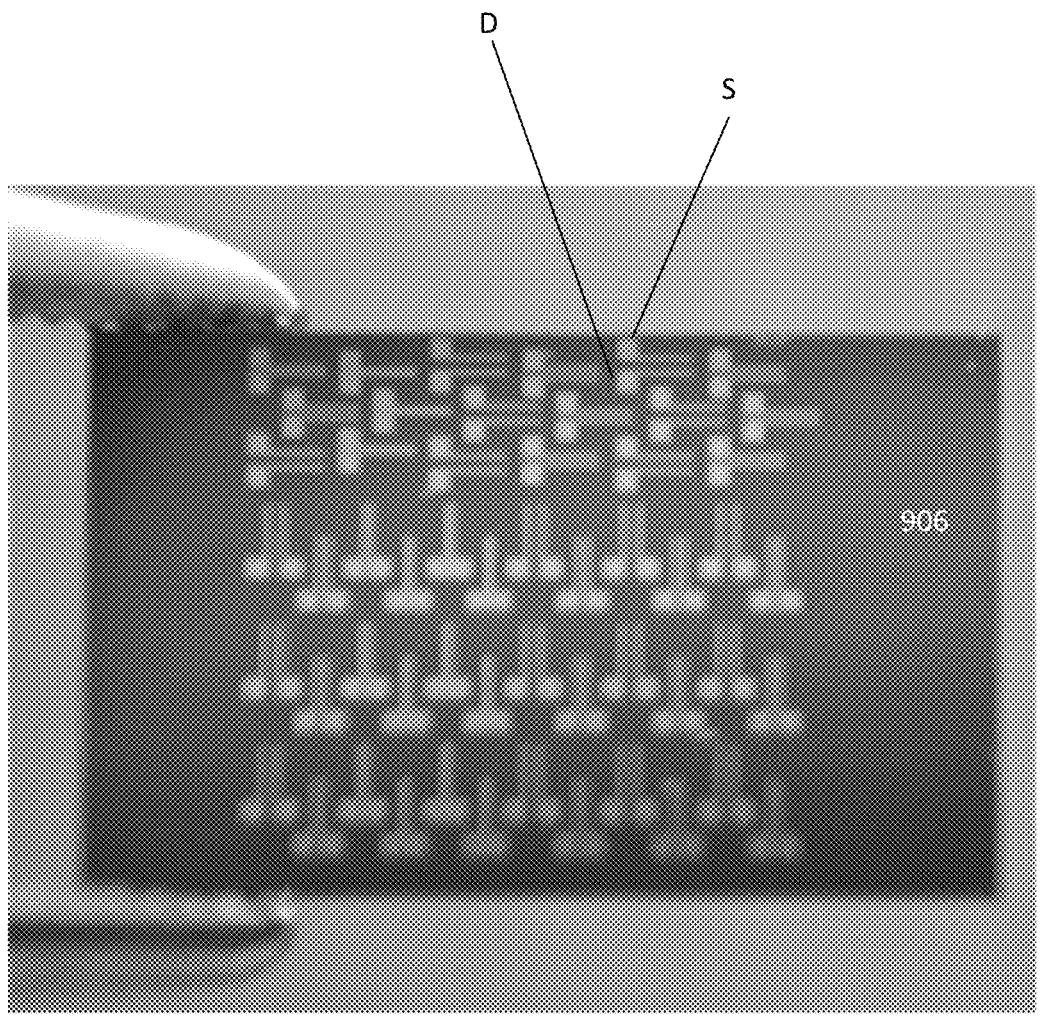
FIG. 10 illustrates a device comprising storage for a plurality of OFETs, including source and drain contacts/connections for the OFETs, according to one or more embodiments of the present invention.

Block 612 represents the end result, a device. In one or more embodiments, the device 800 includes one or more OFETs, e.g., as illustrated in FIG. 9. Each OFET comprises a source contact S and a drain contact D to a film comprising the one or more semiconducting polymers 902; and a gate connection G on a dielectric 904, wherein the gate connection G applies a field to the one or more semiconducting polymers 902 across the dielectric 904 to modulate conduction along one or more backbones of the one or more semiconducting polymers in a channel/active region between the source contact S and the drain contact D.

Embodiments of the present invention are not limited to the particular sequence of depositing the source, drain, and gate contacts. For example, OFETs according to one or more embodiments of the present invention can be fabricated in a bottom gate & top contact geometry, bottom gate & bottom contact geometry, top gate & bottom contact geometry, and top gate & top contact geometry [23].

In one or more embodiments, the semiconducting polymers are stacked into a crystalline structure, wherein the crystalline structure is characterized by observation of a diffraction peak measured by grazing incidence wide-angle X-ray scattering (GIWAXS) of the film.

In one or more embodiments, the fabrication of the OFET, including selection of one or more compositions, one or more structures, and one or more configurations of the source, the drain, the gate, the dielectric, and/or the SAM; selection of a composition, structure (including regioregularity), crystallinity, and/or stability of the semiconducting polymers; selection of the solution casting conditions (e.g., solvent composition, casting speed) and annealing conditions (e.g., annealing time and/or temperature) for fabrication of the film comprising the semiconducting polymers; and selection of the quality and/or morphology of the film, are such that:
- the semiconducting polymers are disposed in a film on a planar, non-grooved surface, wherein the film is characterized by the OFETs each having a hole and/or electron mobility of at least 1.2 $cm^2V^{-1}s^{-1}$ in a saturation regime (e.g., in a range of 1.2-10 $cm^2V^{-1}s^{-1}$); and/or
- mobility of the OFETs is no less than 0.03 $cm^2V^{-1}s^{-1}$ after exposure to the air for between 1 and 5 days; and/or
- the semiconducting polymers comprise polymer chains stacked into film having a crystalline structure, and the crystalline structure is characterized by observation of a diffraction peak measured by grazing incidence wide-angle X-ray scattering (GIWAXS) of the film; and/or
- a π-π distance between adjacent polymer chains is no more than 0.35 nm.

Thus, one or more embodiments of the present invention have discovered that semiconducting polymers with fluoro functionality have unique properties. Specifically, the inventors have unexpectedly and surprisingly discovered that some fluorinated semiconducting polymers with specific fluorine moieties (e.g., P2F or PCDTFBT) can be used to fabricate OFETs having increased stability in air as evidenced by carrier mobility that is less degraded by exposure to air as compared to OFETs fabricated using PCDTPT or PBT. In addition, the inventors have unexpectedly and surprisingly discovered that some fluorinated semiconducting polymers with specific fluorine moieties (e.g., P2F or PCDTFBT) have increased mobility (e.g., 1.2 $cm^2V^{-1}s^{-1}$) as compared to OFETs fabricated using their non-fluorinated counterpart PCDTPT (having a hole mobility of 0.6 $cm^2V^{-1}s^{-1}$ as measured in reference[6]). Thus, the OFET with a P2F (PCDTFBT) channel according to one or more embodiments of the present invention exhibited a 200% higher hole mobility as compared to the OFET with the PCDTPT channel reported in other work[6]. These discoveries are unexpected and surprising at least because OFETs fabricated using some fluorinated polymers (e.g., PDF) had reduced mobility. Moreover, the molecular structure of the fluorinated semiconducting polymers did not appear to have a negative impact on the alkyl chain or π-π stacking distance of the semiconducting polymers.

The relative stability of the fluorinated polymers enables fabrication of devices that could not previously have been envisaged. Specifically, devices where the OFETs are exposed to air can be fabricated. Moreover, much cheaper and simpler packaging that exposes the OFETs to air can be used.

In addition, Applicant's selection of temperature and Br-FBT-Br:M1 ratios during coupling reactions, and M1:M2 ratio during polymerization, lead to surprising and unexpected increases in yield of M2 and the semiconducting polymer, as compared to the yields reported in reference [24].

Device Embodiments

FIG. 9 illustrates a device comprising storage (e.g., a substrate 906 and packaging 908) for a plurality of the OFETs each comprising a source S, drain D, and gate (e.g., at least 8 of the OFETs). The storage/packaging exposes the semiconducting polymers to air. In one or more embodiments, the device 900 comprises an optoelectronic or electronic device storing the OFETs in an electrical/electronic circuit. In one or more embodiments, the OFETs do not comprise encapsulation layers or the semiconducting polymers are covered by layers/encapsulation/packaging permeable to air. In one or more embodiments, the device 900 further comprises electrical connections and/or voltage sources to bias the OFETs with the appropriate threshold voltages and source-drain voltages to achieve the above described desired mobility and/or performance stability, and outputs to receive the outputs from each of the OFETs. In one or more embodiments, the OFETs are connected in a circuit to form logic gates. In one or more embodiments, the device comprises a display or array of sensors comprising the logic gates.

REFERENCES

The following references are incorporated by reference herein.

1 (a) C. D. Dimitrakopoulos and P. R. L. Malenfant, *Adv. Mater.*, 2002, 14, 99-117; (b) A. C. Arias, J. D. MacKenzie, I. McCulloch, J. Rivnay and A. Salleo, *Chem. Rev.*, 2010, 110, 3-24.

2 (a) J. Li, Y. Zhao, H. S. Tan, Y. L. Guo, C. A. Di, G. Yu, Y. Q. Liu, M. Lin, S. H. Lim, Y. H. Zhou, H. B. Su and B. S. Ong, *Sci. Rep.*, 2012, 2, 754-764; (b) I. Kang, H. J. Yun, D. S. Chung, S. K. Kwon and Y. H. Kim, *J. Am. Chem. Soc.*, 2013, 135, 14896-14899; (c) G. Kim, S. J. Kang, G. K. Dutta, Y. K. Han, T. J. Shin, Y. Y. Noh and C. Yang, *J. Am. Chem. Soc.*, 2014, 136, 9477-9483; (d) H. R. Tseng, H. Phan, C. Luo, M. Wang, L. A. Perez, S. N. Patel, L. Ying, E. J. Kramer, T. Q. Nguyen, G. C. Bazan and A. J. Heeger, *Adv. Mater.*, 2014, 26, 2993-2998. (e) Y. Diao, B. C. K. Tee, G. Giri, J. Xu, D. H. Kim, H. A. Becerril, R. M. Stoltenberg, T. H. Lee, G. Xue, S. C. B. Mannsfeld and Z. N. Bao, *Nat. Mater.*, 2013, 12, 665-671. (f) Y. B. Yuan, G. Giri, A. L. Ayzner, A. P. Zoombelt, S. C. B. Mannsfeld, J. H. Chen, D. Nordlund, M. F. Toney, J. S. Huang and Z. N. Bao, *Nat. Commun.*, 2014, 5, 3005.

3 (a) L. Biniek, B. C. Schroeder, C. B. Nielsen and I. McCulloch, *J. Mater. Chem.*, 2012, 22, 14803-14813; (b) J. G. Mei, Y. Diao, A. L. Appleton, L. Fang and Z. N. Bao, *J. Am. Chem. Soc.*, 2013, 135, 6724-6746; (c) Y. Olivier, D. Niedzialek, V. Lemaur, W. Pisula, K. Mullen, U. Koldemir, J. R. Reynolds, R. Lazzaroni, J. Cornil and D. Beljonne, *Adv. Mater.*, 2014, 26, 2119-2136.

4 M. Zhang, H. N. Tsao, W. Pisula, C. D. Yang, A. K. Mishra and K. Müllen, *J. Am. Chem. Soc.*, 2007, 129, 3472-3473.

5 (a) H. N. Tsao, D. Cho, J. W. Andreasen, A. Rouhanipour, D. W. Breiby, W. Pisula and K. Müllen, *Adv. Mater.*, 2009, 21, 209-212; (b) S. H. Wang, M. Kappl, I. Liebewirth, M. Muller, K. Kirchhoff, W. Pisula and K. Müllen, *Adv. Mater.*, 2012, 24, 417-420; (c) Y. Yamashita, J. Tsurumi, F. Hinkel, Y. Okada, J. Soeda, W. Zajaczkowski, M. Baumgarten, W. Pisula, H. Matsui, K. Müllen and J. Takeya, *Adv. Mater.*, 2014, 26, 8169-8173.

6 L. Ying, B. B. Y. Hsu, H. M. Zhan, G. C. Welch, P. Zalar, L. A. Perez, E. J. Kramer, T. Q. Nguyen, A. J. Heeger, W. Y. Wong and G. C. Bazan, *J. Am. Chem. Soc.*, 2011, 133, 18538-18541.

7 (a) R. C. Coffin, J. Peet, J. Rogers and G. C. Bazan, *Nat. Chem.*, 2009, 1, 657-661; (b) C. K. Mai, H. Q. Zhou, Y. Zhang, Z. B. Henson, T. Q. Nguyen, A. J. Heeger and G. C. Bazan, *Angew. Chem. Int. Ed.*, 2013, 52, 12874-12878; (c) Y. Zhang, J. Y. Zou, C. C. Cheuh, H. L. Yip and A. K. Y. Jen, *Macromolecules*, 2012, 45, 5427-5435.

8 (a) D. M. deLeeuw, M. M. J. Simenon, A. R. Brown and R. E. F. Einerhand, *Synth. Met.*, 1997, 87, 53-59; (b) N. Blouin, A. Michaud, D. Gendron, S. Wakim, E. Blair, R. Neagu-Plesu, M. Belletete, G. Durocher, Y. Tao and M. Leclerc, *J. Am. Chem. Soc.*, 2008, 130, 732-742.

9 (a) T. S. van der Poll, J. A. Love, T. Q. Nguyen and G. C. Bazan, *Adv. Mater.*, 2012, 24, 3646-3649; (b) H. Q. Zhou, Y. Zhang, C. K. Mai, J. Seifter, T. Q. Nguyen, G. C. Bazan and A. J. Heeger, *ACS Nano*, 2015, 9, 371-377.

10 (a) K. Takimiya, T. Yamamoto, H. Ebata, T. Izawa, *Sci. Technol. Adv. Mater.*, 2007, 8, 273-276; (b) W. M. Zhang, J. Smith, S. E. Watkins, R. Gysel, M. McGehee, A. Salleo, J. Kirkpatrick, S. Ashraf, T. Anthopoulos, M. Heeney and I. McCulloch, *J. Am. Chem. Soc.*, 2010, 132, 11437-11439.

11 L. A. Perez, P. Zalar, L. Ying, K. Schmidt, M. F. Toney, T. Q. Nguyen, G. C. Bazan and E. J. Kramer, *Macromolecules*, 2014, 47, 1403-1410.

12 H. R. Tseng, L. Ying, B. B. Y. Hsu, L. A. Perez, C. J. Takacs, G. C. Bazan and A. J. Heeger, *Nano Lett.*, 2012, 12, 6353-6357.

13 C. M. Cardona, W. Li, A. E. Kaifer, D. Stockdale and G. C. Bazan, *Adv. Mater.*, 2011, 23, 2367-2371.

14 R. L. Uy, S. C. Price and W. You, *Macromol. Rapid Commun.*, 2012, 33, 1162-1177.

15 S. N. Patel, G. M. Su, C. Luo, M. Wang, L. A. Perez, D. A. Fischer, D. Prendergast, G. C. Bazan, A. J. Heeger, M. L. Chabinyc and E. J. Kramer, *Macromolecules*, 2015, 48, 6606-6616.

16 J. Zaumseil and H. Sirringhaus, *Chem. Rev.*, 2007, 107, 1296-1323.

17 Y. Zhao, Y. L. Guo and Y. Q. Liu, *Adv. Mater.*, 2013, 25, 5372-5391.

18 D. Venkateshvaran, M. Nikolka, A. Sadhanala, V. Lemaur, M. Zelazny, M. Kepa, M. Hurhangee, A. J. Kronemeijer, V. Pecunia, I. Nasrallah, I. Romanov, K. Broch, I. McCulloch, D. Emin, Y. Olivier, J. Cornil, D. Beljonne and H. Sirringhaus, *Nature*, 2014, 515, 384-388.

19 (a) Z. H. Chen, P. Cai, J. W. Chen, X. C. Liu, L. J. Zhang, L. F. Lan, J. B. Peng, Y. G. Ma and Y. Cao, *Adv. Mater.*, 2014, 26, 2586-2591; (b) X. F. Liu, B. B. Y. Hsu, Y. M. Sun, C. K. Mai, A. J. Heeger and G. C. Bazan, *J. Am. Chem. Soc.*, 2014, 136, 16144-16147.

20 H. Bronstein, J. M. Frost, A. Hadipour, Y. Kim, C. B. Nielsen, R. S. Ashraf, B. P. Rand, S. Watkins, I. McCulloch, *Chem. Mater.*, 2013, 25, 277-285.

21 (a) Rivnay, J.; Mannsfeld, S. C.; Miller, C. E.; Salleo, A.; Toney, M. F. *Chem. Rev.*, 2012, 112, 5488-5519; (b) Chabinyc, M. L. *Polym. Rev.*, 2008, 48, 463-492.

22 Supplementary Information entitled "Fluorine Substitution Influence on Benzo[2,1,3]thiodiazole Based Polymers for Field-Effect Transistor Applications," by Ming Wang, Michael Ford, Hung Phan, Jessica Coughlin, Thuc-Quyen Nguyen, and Guillermo C. Bazan, found at pages S-1 to S-13 or pages 6-18 of the priority application for the present application (U.S. Provisional Patent Application 62/253,975).

23. DiBenedetto et. al., Molecular Self-Assembled Monolayers and Multilayers for Organic and Unconventional Inorganic Thin-Film Transistor Applications, Adv. Mater. 2009, 21, 1407-1433 DOI 10.1002/adma.200803267.

24. U.S. Pat. No. 9,605,102.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A composition of matter, comprising a monomer of the structure:

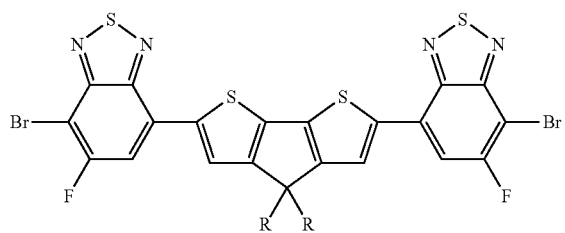

wherein each R is independently hydrogen or a substituted or non-substituted alkyl, aryl or alkoxy chain.

2. A composition of matter, comprising a polymer having the following structure:

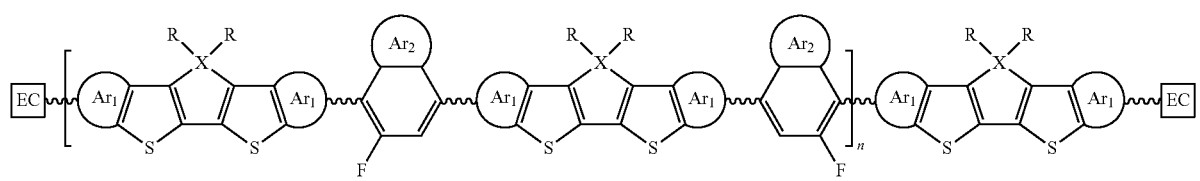

wherein:
each Ar₂ is independently a substituted or non-substituted aromatic functional group containing one, two, three or more aromatic rings, or Ar₂ is independently nothing and the valence of the ring comprising fluorine (F) is completed with hydrogen,
each Ar₁ is independently a substituted or non-substituted aromatic functional group, or each Ar₁ is independently nothing and the valence of its respective thiophene ring is completed with hydrogen,
each R is independently hydrogen or a substituted or non-substituted alkyl, aryl or alkoxy chain;
n is an integer; and
EC is an end capping moiety.

3. The composition of matter of claim 2, wherein EC is an aromatic moiety.

4. The composition of matter of claim 2, wherein the polymer comprises a palladium content of less than 200 parts per million.

5. The composition of matter of claim 2, wherein the polymer has a molecular weight in a range of 45-55 kilodaltons (kDa).

6. The composition of matter of claim 2, wherein the polymer has a molecular weight in a range of 30-80 kDa.

7. The composition of matter of claim 2, wherein the polymer has a molecular weight of 50 kDa.

8. An organic field effect transistor comprising:
a channel including the composition of matter of claim 2,
a source contact to the channel;
a drain contact to the channel; and
a gate contact on or above the channel.

9. A method of fabricating a composition of matter, comprising:
performing a coupling reaction wherein:
a first compound and a second compound are coupled in a solution to form a product, using an excess amount of the second compound as compared to the first compound, and
the first compound comprises a dithiophene and the second compound has the structure:

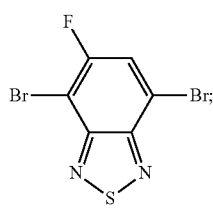 [SMILES: Fc1cc(Br)c2nsnc2c1Br]

and
purifying the product in a solvent mixture to obtain a third compound having the structure (M2):

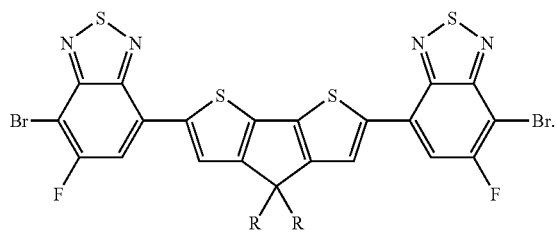

10. The method of claim 9, wherein the excess amount is such that a ratio of the second compound to the first compound is in a range of 1.5-4:1.

11. The method of claim 10, wherein the coupling reaction is performed at a temperature between 50° C. to 130° C.

12. The method of claim 11, wherein the ratio is between 2.2-2.5:1.

13. The method of claim 12, wherein the temperature is in a range between 70° C. and 110° C.

14. The method of claim 9, further comprising:
polymerizing the third compound with the first compound, wherein the first compound is a monomer of the structure (M1):

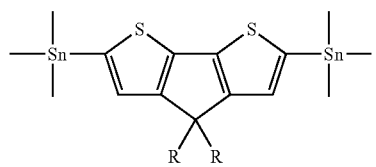

to obtain a semiconducting polymer having a repeating unit of the structure:

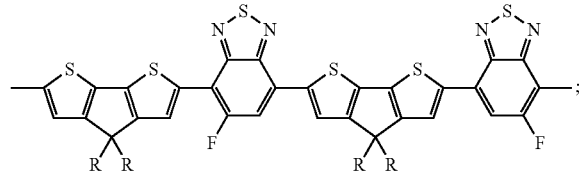

and
wherein:
the fluorine (F) is regioregularly arranged along the semiconducting polymer's conjugated main chain section; and
the R are each independently an alkyl, aryl, or an alkoxy chain.

15. The method of claim 14, further comprising performing the polymerization using a ratio of M1:M2 of 1.15:1.

16. The method of claim 14, further comprising performing the polymerization using a ratio of M1:M2 of less than 1.

17. The method of claim 14, further comprising:
performing the coupling reaction with the excess amount of the second compound and at a temperature;
performing the polymerization using a ratio of M1:M2;
extracting the semiconducting polymer having a molecular weight in a range of 30-80 kDa; and
wherein:
a percentage yield of third compound is at least 60%,
a percentage yield of the semiconducting polymer is at least 70%, and $$\text{percent yield} = \frac{\text{actual yield}}{\text{theoretical yield}} \times 100\%.$$

18. The method of claim 14, further comprising performing an end-capping reaction with aromatic bromide so as to obtain an end capped polymer of the structure:

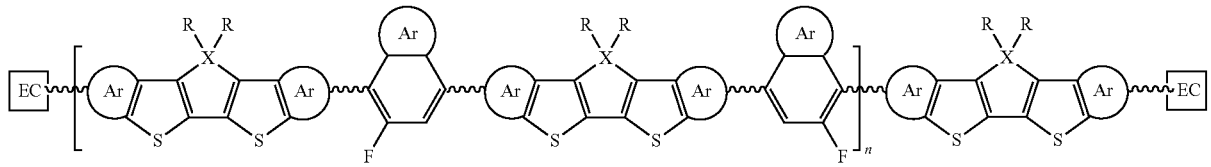

wherein:
each $Ar_2$ is independently a substituted or non-substituted aromatic functional group containing one, two, three or more aromatic rings, or $Ar_2$ is independently nothing and the valence of the ring comprising fluorine (F) is completed with hydrogen,
each $Ar_1$ is independently a substituted or non-substituted aromatic functional group, or each is independently nothing and the valence of its respective thiophene ring is completed with hydrogen,
each R is independently hydrogen or a substituted or non-substituted alkyl, aryl or alkoxy chain;
n is an integer; and
EC is an aromatic moiety of the aromatic bromide.

19. The composition of matter of claim 18, wherein the aromatic bromide is bromobenzene or bromothiophene.

20. The method of claim 18, wherein the end capping is in a presence of a catalyst, the method further comprising:

combining the end capped polymer in solution with sodium diethyldithiocarbamate aqueous solution so as to form a mixture;
heating the mixture;
separating an organic phase from the mixture;
washing the organic phase;
concentrating the organic phase; and
adding the organic phase drop wise to a solvent so as to precipitate a purified form of the end capped polymer.

21. The method of claim 18, wherein the end capping is in a presence of a catalyst, the method further comprising:
passing the end capped polymer in solution through a silica gel column so as to obtain a purified solution;
adding the purified solution drop wise to a solvent so as to precipitate a purified form of the end capped polymer.

* * * * *